US008795976B2

(12) United States Patent
Nakamura et al.

(10) Patent No.: US 8,795,976 B2
(45) Date of Patent: Aug. 5, 2014

(54) GENE AND POLYPEPTIDE RELATING TO BREAST CANCER

(75) Inventors: Yusuke Nakamura, Bunkyo-ku (JP); Toyomasa Katagiri, Bunkyo-ku (JP); Shuichi Nakatsuru, Kawasaki (JP)

(73) Assignee: OncoTherapy Science, Inc. (JP)

( * ) Notice: Subject to any disclaimer, the term of this patent is extended or adjusted under 35 U.S.C. 154(b) by 795 days.

(21) Appl. No.: 11/913,166

(22) PCT Filed: Jul. 26, 2006

(86) PCT No.: PCT/JP2006/315341
§ 371 (c)(1), (2), (4) Date: Jan. 22, 2009

(87) PCT Pub. No.: WO2007/013670
PCT Pub. Date: Feb. 1, 2007

(65) Prior Publication Data

US 2009/0202543 A1 Aug. 13, 2009

Related U.S. Application Data

(60) Provisional application No. 60/703,658, filed on Jul. 29, 2005.

(51) Int. Cl.
*G01N 33/574* (2006.01)

(52) U.S. Cl.
USPC .......................................... 435/7.23; 435/41

(58) Field of Classification Search
None
See application file for complete search history.

(56) References Cited

U.S. PATENT DOCUMENTS

| | | | | |
|---|---|---|---|---|
| 2003/0099974 | A1 | 5/2003 | Lillie et al. | |
| 2004/0029114 | A1 * | 2/2004 | Mack et al. | 435/6 |
| 2004/0191819 | A1 | 9/2004 | Eveleigh et al. | |

FOREIGN PATENT DOCUMENTS

| | | | |
|---|---|---|---|
| EP | 1621637 | A | 2/2006 |
| JP | 2005/503760 | | 2/2005 |
| WO | WO 02/059377 | A2 | 8/2002 |
| WO | WO02059377 | * | 8/2002 |
| WO | WO03073826 | * | 9/2003 |
| WO | WO 2004/078035 | A2 | 9/2004 |
| WO | WO2004078035 | * | 9/2004 |
| WO | WO 2004/094636 | A | 11/2004 |
| WO | 2005/019475 | | 3/2005 |
| WO | 2005/028676 | | 3/2005 |
| WO | 2005/029067 | | 3/2005 |
| WO | WO2006013474 | * | 2/2006 |

OTHER PUBLICATIONS

Sequence search result 2010.*
Sequence search result (WR). 2010.*
Sequence search result (Morris), 2010.*
Sequence search result (Mack), 2010.*
Sequence search result (Eveleigh), 2010.*
Bennett, E.P., et al., "Cloning and characterization of a close homologue of human UDP-N-acetyl-α-D-galactosamine:Polypeptide N-acetylgalactosaminyltranferase-T3, designated GalNAc-T6. Evidence for genetic but not functional redundancy," 1999, *J. Biol. Chem.*, vol. 274(36), pp. 25362-25370.
Marcos, N.T., et al., "Polypeptide GalNAc-transferases, ST6GalNAc-transferase I, and ST3Gal-transferase I expression in gastric carcinoma cell lines," 2003, *J. Histochem. Cytochem.*, vol. 51(6), pp. 761-771.
U.S. Appl. No. 13/392,058, which is a U.S. National Phase of PCT/JP2010/005115, filed Aug. 19, 2010, 67 pgs.

* cited by examiner

*Primary Examiner* — Lei Yao
(74) *Attorney, Agent, or Firm* — Kilpatrick Townsend & Stockton LLP

(57) ABSTRACT

The present application provides novel human gene B7330N whose expression is markedly elevated in breast cancers. The gene and polypeptide encoded by the gene can be used, for example, in the diagnosis of breast cancers, as target molecules for developing drugs against the disease, and for attenuating cell growth of breast cancer.

2 Claims, 10 Drawing Sheets c d a b c

GENE AND POLYPEPTIDE RELATING TO BREAST CANCER

CROSS-REFERENCE TO RELATED APPLICATIONS

This application is a U.S. National Stage Application of PCT/JP2006/315341, filed Jul. 26, 2006, which claims the benefit of U.S. Provisional Application Ser. No. 60/703,658 filed Jul. 29, 2005, all of which are hereby incorporated by reference in their entirety.

TECHNICAL FIELD

The present invention relates to the field of biological science, more specifically to the field of cancer therapy and diagnosis. In particular, the present invention relates to novel polypeptides encoded by a novel gene B7330N relating to breast cancer. Furthermore, the present invention relates to the novel gene B7330N. The genes and polypeptides of the present invention can be used, for example, in the diagnosis of breast cancer, as target molecules for developing drugs against the disease, and for attenuating cell growth of breast cancer.

BACKGROUND ART

Breast cancer, a genetically heterogeneous disease, is the most common malignancy in women. An estimation of approximately 800000 new cases were reported each year worldwide (Parkin D M, et al., 1999, CA Cancer J Clin 49: 33-64). Mastectomy is the first concurrent option for the treatment of this disease. Despite surgical removal of the primary tumors, relapse at local or distant sites may occur due to undetectable micrometastasis (Saphner T, et al., 1996, J Clin Oncol, 14, 2738-46) at the time of diagnosis. Cytotoxic agents are usually administered as adjuvant therapy after surgery aiming to kill those residual or pre malignant cells.

Treatment with conventional chemotherapeutic agents is often empirical and is mostly based on histological tumor parameters, and in the absence of specific mechanistic understanding. Target-directed drugs are therefore becoming the bedrock treatment for breast cancer. Tamoxifen and aromatase inhibitors, two representatives of its kind, have been proved to have great responses used as adjuvant or chemoprevention in patients with metastasized breast cancer (Fisher B, et al., (1998) J Natl Cancer Inst, 90, 1371-88; Cuzick J, et al., (2002) Lancet 360, 817-24). However the drawback is that only patients expressed estrogen receptors are sensitive to these drugs. A recent concerns were even raised regarding their side effects particularly lay on the possibility of causing endometrial cancer for long term tamoxifen treatment as well as deleterious effect of bone fracture in the postmenopausal women in aromatase prescribed patients (Coleman R E, et al., (2004) Oncology. 18 (5 Suppl 3), 16-20).

Owing to the emergence of side effect and drug resistance, it is obviously necessarily to search novel molecular targets for selective smart drugs on the basis of characterized mechanisms of action. To achieve this goal, we have been analyzing the expression profiles of 77 breast tumors, including 8 DCISs and 69 IDCs purified by means of a combination of a laser-microbeam microdissection (LMM) and a cDNA microarray representing 27,648 genes. The data from these experiments not only should provide important information about breast tumorigenesis, but also are invaluable for identifying candidate genes whose products might serve as diagnostic markers and/or as molecular targets for treatment of breast cancer.

In this invention we isolated a novel gene, B7330N that was significantly overexpressed in breast cancer cells through the expression profile of breast cancer, and further confirmed that B7330N was overexpressed in breast cancer cells by semi-quantitative RT-PCR and Northern blot analyses. We demonstrated that treatment of breast cancer cells with siRNAs effectively inhibited expression of B7330N and suppressed cell/tumor growth of breast cancer. Take together, we suggest B7330N, also designated as GALNT6, as a prominent novel molecular candidate for diagnostic markers and breast cancer drug development.

Studies designed to reveal mechanisms of carcinogenesis have already facilitated identification of molecular targets for anti-tumor agents. For example, inhibitors of farnesyltransferase (FTIs) which were originally developed to inhibit the growth-signaling pathway related to Ras, whose activation depends on posttranslational farnesylation, has been effective in treating Ras-dependent tumors in animal models (Sun J, et al., Oncogene 16: 1467-73 (1998)). Clinical trials on human using a combination or anti-cancer drugs and anti-HER2 monoclonal antibody, trastuzumab, have been conducted to antagonize the protooncogene receptor HER2/neu; and have been achieving improved clinical response and overall survival of breast cancer patients (Molina M A, et al., Cancer Res 61:4744-4749 (2001)). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (O'Dwyer M E and Druker B J, Curr Opin Oncol 12:594-7 (2000)). Therefore, gene products commonly up-regulated in cancerous cells may serve as potential targets for developing novel anti-cancer agents.

It has been demonstrated that CD8+ cytotoxic T lymphocytes (CTLs) recognize epitope peptides derived from tumor-associated antigens (TAAs) presented on MHC Class I molecule, and lyse tumor cells. Since the discovery of MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (199.1); Brichard et al., J Exp Med 178: 489-95 (1993); Kawakami et al., J Exp Med 180: 347-52 (1994)). Some of the discovered TAAs are now in the stage of clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products which had been demonstrated to be specifically over-expressed in tumor cells, have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenberg et al., Nature Med 4: 321-7 (1998); Mukheiji et al., Proc Natl Acad Sci USA 92: 8078-82 (1995); Hu et al., Cancer Res 56: 2479-83 (1996)), only limited number of candidate TAAs for the treatment of adenocarcinomas, including colorectal cancer, are available.

TAAs abundantly expressed in cancer cells, and at the same time which expression is restricted to cancer cells would be promising candidates as immunotherapeutic targets. Further, identification of new TAAs inducing potent and specific anti-tumor immune responses is expected to encourage clinical use of peptide vaccination strategy in various types of cancer (Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-55 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., hit J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res. 92: 762-7 (2001)). However, both of BLA-A24 and HLA-A0201 are one of the common HLA alleles in Japanese, as well as Caucasian populations (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Histocompatibility Workshop and Conference Oxford University Press, Oxford, 1065 (1992); Williams et al., Tissue Antigen 49: 129 (1997)). Thus, antigenic peptides of cancers presented by these HLAs may be especially useful for the treatment of cancers among Japanese and Caucasian populations. Further, it is known that the induction of low-affinity CTL in vitro usually results from the use of peptide at a high concentration, generating a high level of specific peptide/NHC complexes on antigen presenting cells (APCs), which will effectively activate these CTL (Alexander-Miller et al., Proc Natl Acad Sci USA 93: 4102-7 (1996)).

SUMMARY OF THE INVENTION

To isolate novel molecular targets for treatments of breast cancer, we investigated precise genome-wide expression profiles of 77 cases with premenopausal breast cancer by using a combination of cDNA microarray and laser microbeam microdissection. Among the up-regulated gene, we identified B7330N, also designated as UDP-N-acetyl-alpha-D-galactosamine: polypeptide N-acetylgalactosaminyltransferase 6 (GALNT6), that was more than three-fold overexpressed in 27 of 77 (35%) breast cancer cases from which we were able to obtain expression data. Subsequent semi-quantitative RT-PCR also confirmed that B7330N were up-regulated in 7 of 12 clinical breast cancer samples and 7 of 20 breast cancer cell lines, compared to normal human organs including breast ductal cells or normal breast. Northern blot analyses revealed that the B7330N transcript was expressed only in breast cancer cell lines and normal human placenta, pancreas, stomach, trachea, mammary gland and bone marrow. Immunocytochemical staining shows that subcellular localization of exogenous B7330N was appeared as a granulous pattern in secretion vesicles in COS7 cells. Induction of B7330N cDNA into COS7 cells led to secretion of the gene product into culture media and resulted in enhancement of cell growth. Treatment of breast cancer cells with small interfering RNAs (siRNAs) effectively inhibited expression of B7330N and suppressed cell/tumor growth of breast cancer cell lines, T47D and BT-20, suggesting that this gene plays a key role in cell growth proliferation with autocrine manner. The combined evidence suggests that B7330N represents a promising candidate for development of molecular-targeting therapy and could serve as a prominent diagnostic tumor-marker for patients with breast cancer.

B7330N encodes a 622-amino acid protein. According to a Northern blot analysis, the expression of B7330N was shown to be restricted to breast cancer cell lines and normal human placenta, pancreas, stomach, trachea, mammary gland and bone marrow.

Many anticancer drugs are not only toxic to cancer cells but also for normally growing cells. However, agents suppressing the expression of B7330N may not adversely affect other organs due to the fact that normal expression of B7330N is restricted to placenta, pancreas, stomach, trachea, mammary gland and bone marrow, and thus may be conveniently used for treating or preventing breast cancer.

Thus, the present invention provides an isolated gene, B7330N, which serves as a candidate of diagnostic markers for breast cancer as well as promising potential targets for developing new strategies for diagnosis and effective anti-cancer agents. Furthermore, the present invention provides a polypeptide encoded by this gene, as well as the production and the use of the same. More specifically, the present invention provides novel human polypeptide, B7330N or a functional equivalent thereof, which expressions are elevated in breast cancer cells.

In a preferred embodiment, the B7330N polypeptide includes a 622 amino acid protein encoded by the open reading frame of SEQ ID NO: 24 or 26. The B7330N polypeptide preferably includes the amino acid sequence set forth in SEQ ID NO: 25. The present application also provides an isolated protein encoded from at least a portion of the B7330N polynucleotide sequence, or polynucleotide sequences at least 15% and more preferably at least 25% complementary to the sequence set forth in SEQ ID NO: 24 or 26.

The present invention further provides a novel human gene B7330N whose expressions is markedly elevated in a great majority of breast cancers as compared to corresponding non-cancerous breast duct epithelium. The isolated B7330N gene includes a polynucleotide sequence as described in SEQ ID NO: 24 or 26. In particular, the B7330N cDNA includes 4381 or 4556 nucleotides that contain an open reading frame of 1869 nucleotides (SEQ ID NO: 24 or 26). The present invention further encompasses polynucleotides which hybridize to and which are at least 15% and more preferably at least 25% complementary to the polynucleotide sequence set forth in SEQ ID NO: 24 or 26, to the extent that they encode a B7330N protein or a functional equivalent thereof. Examples of such polynucleotides are degenerates and allelic mutants of B7330N encoded by the sequence of SEQ ID NO: 24 or 26.

As used herein, an isolated gene is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO: 24 or 26. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence shown in SEQ ID NO: 24 or 26. In the case of an isolated polynucleotide which is longer than or equivalent in length to the reference sequence, e.g., SEQ ID NO: 24 or 26, the comparison is made with the full length of the reference sequence. Where the isolated polynucleotide is shorter than the reference sequence, e.g., shorter than SEQ ID NO: 24 or 26, the comparison is made to a segment of the reference sequence of the same length (excluding any loop required by the homology calculation).

The present invention also provides a method of producing a protein by transfecting or transforming a host cell with a polynucleotide sequence encoding the B7330N protein, and expressing the polynucleotide sequence. In addition, the present invention provides vectors comprising a nucleotide sequence encoding the B7330N protein, and host cells harboring a polynucleotide encoding the B7330N protein. Such vectors and host cells may be used for producing the B7330N protein.

A binding agent that specifically recognizes the B7330N protein is also provided by the present application. For example, a binding agent may be an antibody raised against a B7330N protein. Alternatively, a binding agent may be a ligand specific for the protein, or a synthetic polypeptide that specifically binds the protein (see e.g., WO2004044011). An antisense polynucleotide (e.g., antisense DNA), ribozyme, and siRNA (small interfering RNA) of the B7330N gene is also provided.

The present invention further provides a method for diagnosis of breast cancer which includes the step of determining an expression level of the gene in a biological sample from a subject, comparing the expression level of B7330N gene with that in a normal sample, and defining that a high expression level of the B7330N gene in the sample indicates that the subject suffers from or is at risk of developing breast cancer.

Further, a method of screening for a compound for treating or preventing breast cancer is provided by the present invention. The method includes contacting the B7330N polypeptide with test compounds, and selecting test compounds that bind to or that inhibit the biological activity of the B7330N polypeptide.

The present invention further provides a method of screening for a compound for treating or preventing breast cancer, wherein the method includes contacting a test compound with a cell expressing the B7330N polypeptide or introduced with a vector comprising the transcriptional regulatory region of B7330N upstream of a reporter gene, and selecting the test compound that suppresses the expression level or activity of the reporter gene.

The present invention also provides a method of screening for a compound for treating or preventing breast cancer, wherein the method includes contacting a test compound with a B7330N polypeptide, or cell expressing the B7330N polypeptide, and selecting the test compound that suppresses the glycosylation level of the B7330N polypeptide. In these embodiments, the glycosylation level is that of asparagine 476 of B7330N polypeptide.

The present application also provides a pharmaceutical composition for treating or preventing breast cancer. The pharmaceutical composition may be, for example, an anti-cancer agent. The pharmaceutical composition can comprise at least a portion of antisense S-oligonucleotides, siRNA molecules or ribozymes against the B7330N polynucleotide sequence shown and described in SEQ ID NO: 24 or 26, respectively. A suitable siRNA targets are a sequence of SEQ ID NOs: 18 or 22. Thus, an siRNA of the invention comprises a nucleotide sequence from SEQ ID NOs: 18 or 22. This may be preferably selected as targets for treating or preventing breast cancer according to the present invention. The pharmaceutical compositions may be also those comprising the compounds selected by the present methods of screening for compounds for treating or preventing cell proliferative diseases such as breast cancer.

The course of action of the pharmaceutical composition is desirably to inhibit growth of the cancerous cells such as breast cancer cells. The pharmaceutical composition may be applied to mammals including humans and domesticated mammals.

The present invention further provides methods for treating or preventing breast cancer using the pharmaceutical composition provided by the present invention.

In addition, the present invention provides method for treating or preventing cancer, which method comprises the step of administering the B7330N polypeptide. It is expected that anti tumor immunity is induced by the administration of the B7330N polypeptide. Thus, the present invention also provides method for inducing anti tumor immunity, which method comprises the step of administering the B7330N polypeptide, as well as pharmaceutical composition for treating or preventing cancer comprising the B7330N polypeptide.

It is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 2(*b*) shows exogenous expression of B7330N proteins by Western blot analysis.

FIG. 3(*b*) shows western blot analysis with wild-type B7330N, N476A mutant, and N611A mutant in cell lysates. FIG. 3(*c*) shows effect of N-glycosylation on secretion of B7330N protein.

FIG. 4(*a*) shows semi-quantitative RT-PCR showing suppression of endogenous expression of B7330N in breast cancer cell lines, T47D and BT-20. GAPDH was used as an internal control. FIG. 4(*b*) shows MTT assay demonstrating a decrease in the numbers of colonies by knockdown of B7330N in T47D cells and BT-20 cells. FIG. 4(*c*) shows colony-formation assay demonstrating a decrease in the numbers of colonies by knockdown of B7330N in T47D cells and BT-20 cells.

DETAILED DESCRIPTION OF THE INVENTION

Figure 1:
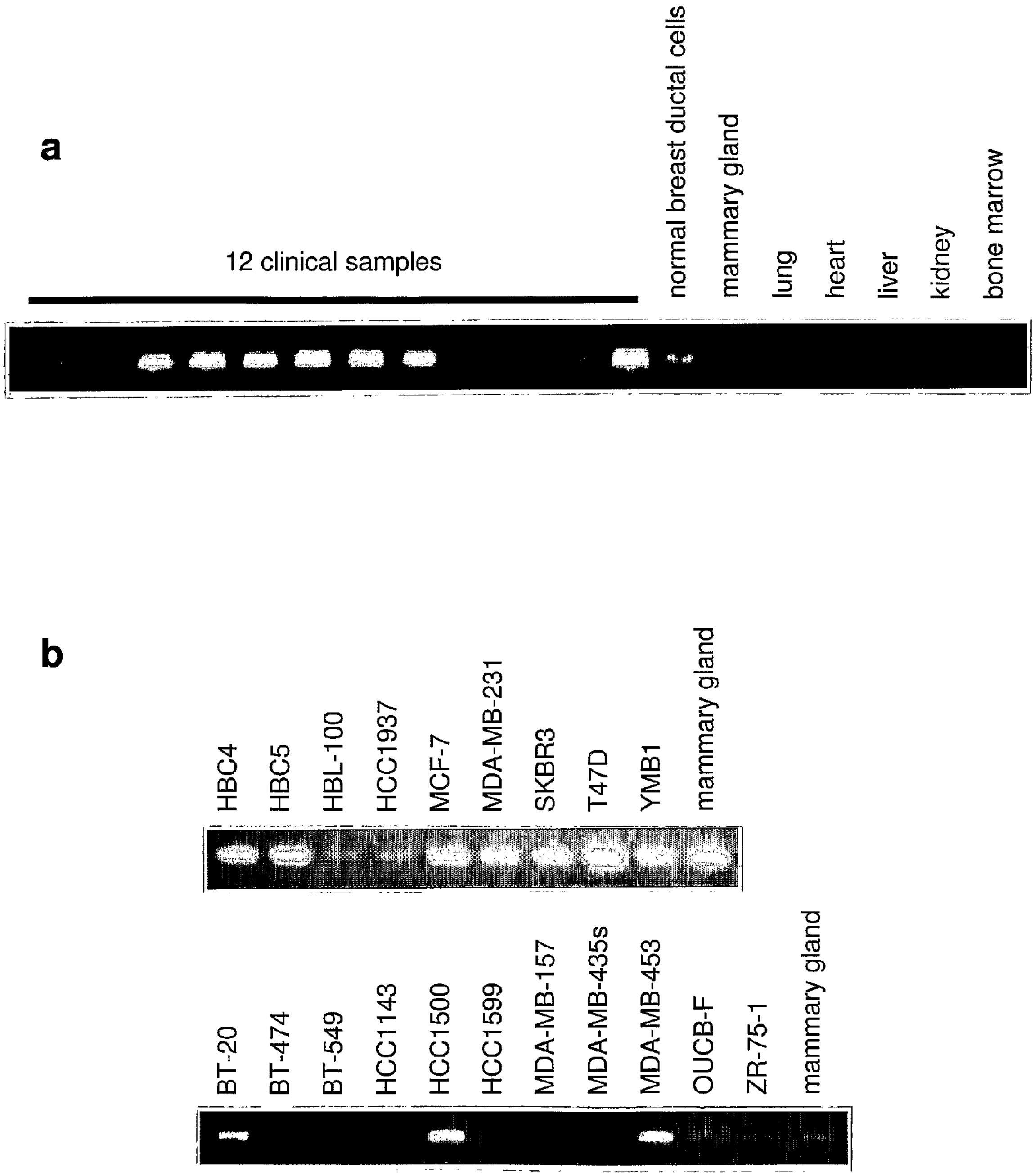
FIG. 1 shows semi-quantitative RT-PCR and northern blot analyses results. Expression of B7330N in (a) tumor cells from breast cancer patients and normal human tissues, (b) breast cancer cell lines; HBC4, HBC5, HBL-100, HCC1937, MCF-7, MDA-MB-231, SKBR3, T47D, YMB1 (upper panel), BT-20, BT-474, BT-549, HCC1143, HCC1500, HCC1599, MDA-MB-157, MDA-MB-435s, MDA-MB-453, OCUCB-F and ZR-75-1 (lower panel) and mammary gland. Northern blot analyses of B7330N transcripts in various human tissues (c), and breast cancer cell lines and normal human vital organs (d).
Figure 1:
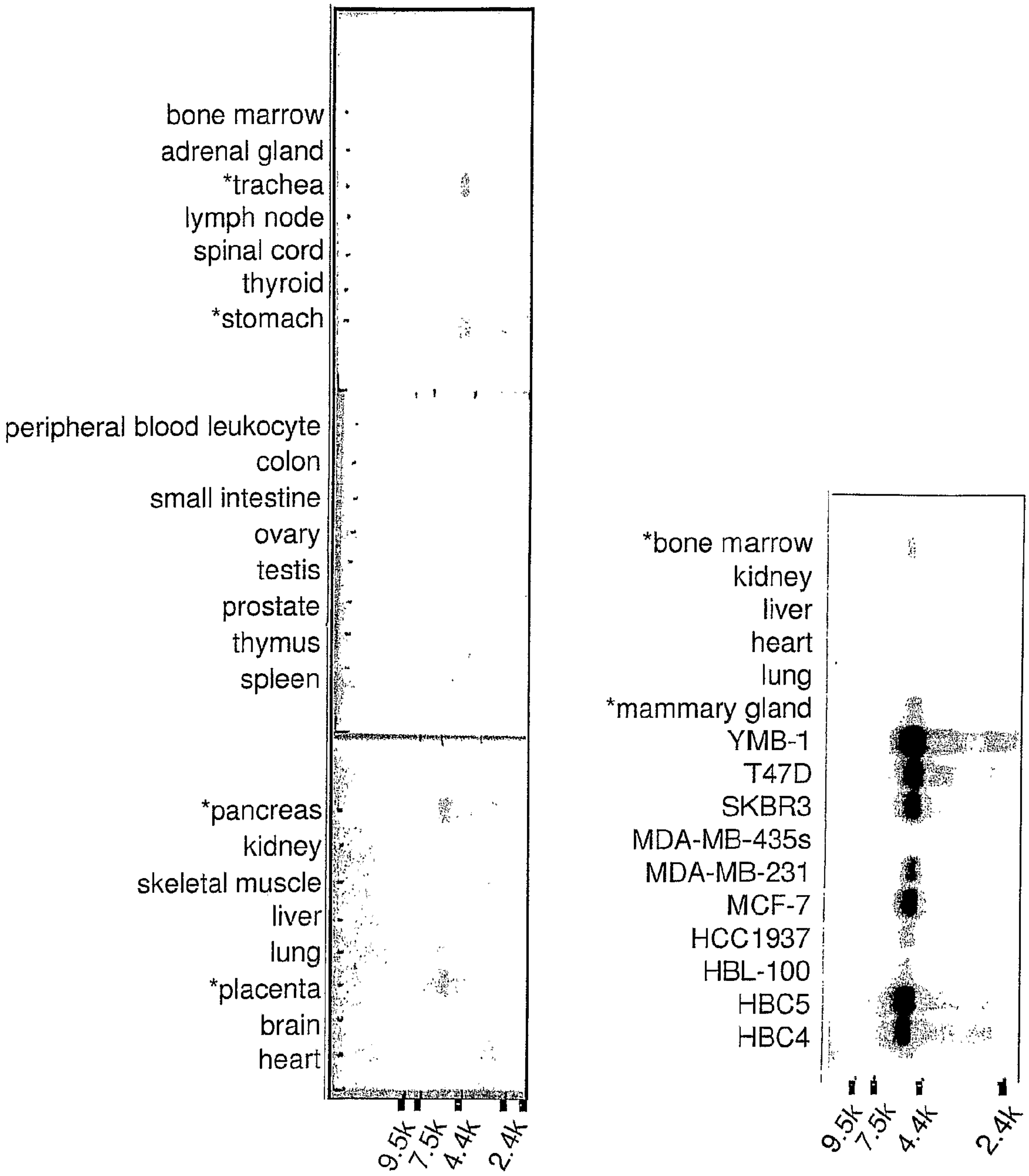

The words "a", "an" and "the" as used herein mean "at least one" unless otherwise specifically indicated. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

To disclose the mechanism of breast cancer and identify novel diagnostic markers and/or drug targets for the treatment and/or prevention of these tumors, the present inventors analyzed the expression profiles of genes in breast cancer using a genome-wide cDNA microarray combined with a laser microbeam microdissection. As a result, B7330N specifically over-expressed in breast cancer cells was identified. Furthermore, suppression of the expression of B7330N gene with small interfering RNAs (siRNAs) resulted in a significant growth-inhibition of cancerous cells. These findings suggest that B7330N render oncogenic activities to cancer cells, and that inhibition of the activity of these proteins could be a promising strategy for the treatment and prevention of proliferative diseases such as breast cancers.

B7330N

The present invention provides B733 ON gene. The cDNA of B7330N consists of 4381 or 4556 nucleotides containing an open reading frame of 1869 nucleotides (SEQ ID NO: 24 or 26; GenBank Accession No. AB265820). These open reading frames encode a 622 amino acid-protein.

Thus, the present invention provides substantially pure polypeptides encoded by these genes including polypeptides comprising the amino acid sequence of SEQ ID NO: 25, as well as functional equivalents thereof, to the extent that they encode a B7330N protein. Examples of polypeptides functionally equivalent to B7330N include, for example, homologous proteins of other organisms corresponding to the human B7330N protein, as well as mutants of human B7330N proteins.

In the present invention, the term "functionally equivalent" means that the subject polypeptide has the activity to promote cell proliferation like the B7330N protein and to confer oncogenic activity to cancer cells. Whether the subject polypeptide has a cell proliferation activity or not can be judged by introducing the DNA encoding the subject polypeptide into a cell, expressing the respective polypeptide and detecting promotion of proliferation of the cells or increase in colony forming activity. Such cells include, for example, NIH3T3, COS7 and BEK293.

Methods for preparing polypeptides functionally equivalent to a given protein are well known by a person skilled in the art and include known methods of introducing mutations into the protein. For example, one skilled in the art can prepare polypeptides functionally equivalent to the human B7330N protein by introducing an appropriate mutation in the amino acid sequence of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-56 (1984); Kramer and Fritz, Methods Enzymol 154: 350-67 (1987); Kunkel, Proc Natl Acad Sci USA 82: 488-92 (1985); Kunkel, et al., Methods Enzymol 204: 125-39 (1991)). Amino acid mutations can occur in nature, too. The polypeptide of the present invention includes those proteins having the amino acid sequences of the human B7330N protein in which one or more amino acids are mutated, provided the resulting mutated polypeptides are functionally equivalent to the human B7330N protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting, deleting, inserting and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

In the present invention, a preferable functional equivalent of the B7330N protein conserves a glycosylation site thereof. For example, it was confirmed that B7330N protein was glycosylated at 476N. Accordingly, in the preferable embodiments, a functional equivalent of B7330N protein consists of an amino acid sequence comprising 476N or homologous to the 476N in a homologous sequence. The amino acid sequence of the functional equivalent of a B7330N protein, a position homologous to the $476^{th}$ position can be determined by comparing the amino acid sequences. The position in a protein of interest needs not necessarily be the $476^{th}$ position. For example, in the case of a protein having the structure of the B7330N protein that has been modified by, for example, an addition, insertion, and/or deletion of one or more amino acids, the homologous position may be a position other than the $476^{th}$ position. In such a protein, to determine a position homologous to the $476^{th}$ position in the B7330N protein, amino acid sequences of both proteins are aligned so as to match mutual amino acids as well as amino acids having similar properties as much as possible by inserting appropriate gaps in both amino acid sequences if necessary. Thus, it can be determined which position in a protein of interest corresponds to a position homologous to the $476^{th}$ position in the B7330N protein. Such a technique has been known among those skilled in the art, and can be performed easily using commercially available or published computer software, for example, the analytical software GENETYX-MAC VER. 10 (Software), etc.

An example of a polypeptide to which one or more amino acids residues are added to the amino acid sequence of human B7330N protein is a fusion protein containing the human B7330N protein. Fusion proteins, fusions of the human B7330N protein and other peptides or proteins, are included in the present invention. Fusion proteins can be made by techniques well known to a person skilled in the art, such as by linking the DNA encoding the human B7330N, protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-10 (1988)), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment and the like. Examples of proteins that may be fused to a protein of the invention include GST (glutathione-S-transferase), Influenza agglutinin (HA), immunoglobulin constant region, β-galactosidase, MBP (maltose-binding protein) and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human B7330N protein (i.e., SEQ ID NO: 24 or 26), and isolate functionally equivalent polypeptides to the human B7330N protein from the isolated DNA. The polypeptides of the present invention include those that are encoded by DNA that hybridizes with a whole or part of the DNA sequence encoding the human B7330N protein and are functionally equivalent to the human B7330N protein. These polypeptides include mammal homologues corresponding to the protein derived from human (for example, a polypeptide encoded by a monkey, rat, rabbit and bovine gene). In isolating a cDNA highly homologous to the DNA encoding the human B7330N protein from animals, it is particularly preferable to use tissues from breast cancer cell and normal human placenta, pancreas, stomach, trachea, mammary gland and bone marrow.

The condition of hybridization for isolating a DNA encoding a polypeptide functionally equivalent to the human B7330N protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human B7330N protein, using a primer synthesized based on the sequence information of the protein encoding DNA (SEQ ID NO: 24 or 26).

Polypeptides that are functionally equivalent to the human B7330N protein encoded by the DNA isolated through the above hybridization techniques or gene amplification techniques normally have a high homology to the amino acid sequence of the human B7330N protein. "High homology" typically refers to a homology of 40% or higher, preferably 60% or higher, more preferably 80% or higher, even more preferably 85%, 90%, 93%, 95%, 98%, 99% or higher between a polypeptide sequence or a polynucleotide sequence and a reference sequence. Percent homology (also referred to as percent identity) is typically carried out between two optimally aligned sequences. Methods of alignment of sequences for comparison are well-known in the art. Optimal alignment of sequences and comparison can be conducted, e.g., using the algorithm in "Wilbur and Lipman, Proc Natl Acad Sci USA 80: 726-30 (1983)".

A polypeptide of the present invention has variations in amino acid sequence, molecular weight, isoelectric point, the presence or absence of sugar chains, or form, depending on the cell or host used to produce it or the purification method utilized. Nevertheless, so long as it has a function equivalent to that of the human B7330N protein of the present invention, it is within the scope of the present invention.

The polypeptide of the present invention can be prepared as recombinant protein or natural protein, by methods well known to those skilled in the art. A recombinant protein can be prepared by inserting a DNA, which encodes the polypeptide of the present invention (for example, the DNA comprising the nucleotide sequence of SEQ ID NO: 24 or 26), into an appropriate expression vector, introducing the vector into an appropriate host cell, obtaining the extract, and purifying the polypeptide by subjecting the extract to chromatography, e.g., ion exchange chromatography, reverse phase chromatography, gel filtration or affinity chromatography utilizing a column to which antibodies against the protein of the present invention is fixed or by combining more than one of aforementioned columns.

Also when the polypeptide of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines or FLAG, it can be detected and purified using antibodies to c-myc, H is or FLAG, respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the B7330N protein described below are bound, with the extract of tissues or cells expressing the polypeptide of the present invention. The antibodies can be polyclonal antibodies or monoclonal antibodies.

The present invention also encompasses partial peptides of the polypeptide of the present invention. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, and screening for inhibitors of the polypeptide of the present invention.

A partial peptide of the invention can be produced by genetic engineering, by known methods of peptide synthesis or by digesting the polypeptide of the invention with an appropriate peptidase. For peptide synthesis, for example, solid phase synthesis or liquid phase synthesis may be used.

The present invention further provides polynucleotides that encode such B7330N polypeptides described above. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention includes a DNA comprising a given nucleotide sequences as well as its degenerate sequences, so long as the resulting DNA encodes a polypeptide of the present invention.

The polynucleotide of the present invention can be prepared by methods known to a person skilled in the art. For example, the polynucleotide of the present invention can be prepared by: preparing a cDNA library from cells which express the polypeptide of the present invention, and conducting hybridization using a partial sequence of the DNA of the present invention (for example, SEQ ID NO: 24 or 26) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 24 or 26), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue or organ (e.g., breast cancer cell and normal human placenta, pancreas, stomach, trachea, mammary gland and bone marrow) in which the object polypeptide of the invention is expressed. Known methods can be used to isolate mRNAs; for instance, total RNA may be prepared by guanidine ultracentrifugation (Chirgwin et al., Biochemistry 18:5294-9 (1979)) or AGPC method (Chomczynski and Sacchi, Anal Biochem 162:156-9 (1987)). In addition, mRNA may be purified from total RNA using mRNA Purification Kit (Pharmacia) and such. Alternatively, mRNA may be directly purified by QuickPrep nRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaka Kogyo). Alternatively, cDNA may be synthesized and amplified following the 5'-RACE method (Frohman et al., Proc Natl Acad Sci USA 85: 8998-9002 (1988); Belyavsky et al., Nucleic Acids Res. 17: 2919-32 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res. 9: 43-74 (1981)). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA or TAG).

Specifically, the polynucleotide of the present invention encompasses the DNA comprising the nucleotide sequence of SEQ ID NO: 24 or 26.

Furthermore, the present invention provides a polynucleotide that hybridizes under stringent conditions with a polynucleotide having a nucleotide sequence of SEQ ID NO: 24 or 26, and encodes a polypeptide functionally equivalent to the B7330N protein of the invention described above. One skilled in the art may appropriately choose stringent conditions. For example, low stringent condition can be used. More preferably, high stringent condition can be used. These conditions are the same as that described above. The hybridizing DNA above is preferably a cDNA or a chromosomal DNA.

The present invention also provides a polynucleotide which is complementary to the polynucleotide encoding human B7330N protein (SEQ ID NO: 24 or 26) or the complementary strand thereof, and which comprises at least 15 nucleotides. The polynucleotide of the present invention is preferably a polynucleotide which specifically hybridizes with the DNA encoding the B7330N polypeptide of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

Vectors and Host Cells

The present invention also provides a vector and host cell into which a polynucleotide of the present invention is introduced. A vector of the present invention is useful to keep a polynucleotide, especially a DNA, of the present invention in host cell, to express the polypeptide of the present invention, or to administer the polynucleotide of the present invention for gene therapy.

When *E. coli* is a host cell and the vector is amplified and produced in a large amount in *E. coli* (e.g., JM109, DH5α, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT and pT7 can also be used for subcloning and extracting cDNA as well as the vectors described above. When a vector is used to produce the protein of the present invention, an expression vector is especially useful. For example, an expression vector to be expressed in *E. coli* should have the above characteristics to be amplified in *E. coli*. When *E. coli*, such as JM109, DH5a, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the *E. coli* is the pelB signal sequence (Lei et al., J. Bacteriol. 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEF-BOS (Mizushima S and Nagata S., Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EFla promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Producing Polypeptides

In addition, the present invention provides methods for producing a polypeptide of the present invention. The polypeptides may be prepared by culturing a host cell which harbors an expression vector comprising a gene encoding the polypeptide. According to needs, methods may be used to express a gene stably and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified polypeptides prepared by the above methods.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase and so on.

Antibodies

The present invention provides an antibody that binds to the polypeptide of the invention. The antibody of the invention can be used in any form, such as monoclonal or polyclonal antibodies, and includes antiserum obtained by immunizing an animal such as a rabbit with the polypeptide of the invention, all classes of polyclonal and monoclonal antibodies, human antibodies and humanized antibodies produced by genetic recombination.

A polypeptide of the invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention.

Herein, an antibody is defined as a protein that reacts with either the full length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates or a chemically synthesized polypeptide may be used as the antigen.

Any mammalian animal may be immunized with the antigen, but preferably the compatibility with parental cells used for cell fusion is taken into account. In general, animals of Rodentia, Lagomorpha or Primates are used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the polypeptide of the present invention is coupled. The antibody of the present invention can be used not only for purification and detection of the polypeptide of the present invention, but also as a candidate for agonists and antagonists of the polypeptide of the present invention. In addition, this antibody can be applied to the antibody treatment for diseases related to the polypeptide of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells or their lysates. Antibody producing cells are then collected from the animals and fused with myeloma cells to obtain hybridoma, from which human antibodies against the polypeptide can be prepared (see WO92-03918, WO94-02602, WO94-25585, WO96-33735 and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, $F(ab')_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see e.g., Verhoeyen et al., *Science* 239: 1534-6 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, J. Mol. Biol. 227:381 (1992)). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

Antisense Polynucleotides, Small Interfering RNAs and Ribozymes

The present invention includes an antisense oligonucleotide that hybridizes with any site within the nucleotide sequence of SEQ ID NO: 24 or 26. This antisense oligonucleotide is preferably against at least about 15 continuous nucleotides of the nucleotide sequence of SEQ ID NO: 24 or 26. The above-mentioned antisense oligonucleotide, which contains an initiation codon in the above-mentioned at least 15 continuous nucleotides, is even more preferred.

Derivatives or modified products of antisense oligonucleotides can also be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term “antisense oligonucleotides” as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 24 or 26.

Such polynucleotides are contained as those having, in the “at least about 15 continuous nucleotide sequence region”, a homology of at least 70% or higher, preferably at 80% or higher, more preferably about 90% or higher, even more preferably about 95% or higher. The algorithm stated herein can be used to determine the homology. Algorithms known in the art can be used to determine the homology. Furthermore, derivatives or modified products of the antisense-oligonucleotides can also be used as antisense-oligonucleotides in the present invention. Examples of such modified products include lower alkyl phosphonate modifications such as methyl-phosphonate-type or ethyl-phosphonate-type, phosphorothioate modifications and phosphoroamidate modifications.

Such antisense polynucleotides are useful as probes for the isolation or detection of DNA encoding the polypeptide of the invention or as a primer used for amplifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA and inhibiting the expression of the polypeptide of the invention, thereby resulting in the inhibition of the polypeptide’s function.

The present invention also includes small interfering RNAs (siRNA) comprising a combination of a sense strand nucleic acid and an antisense strand nucleic acid of the nucleotide sequence of SEQ ID NO: 24 or 26. More specifically, such siRNA for suppressing the expression of B7330N include those that target the nucleotide sequence of SEQ ID NOs: 18 or 22.

The term “siRNA” refers to a double stranded RNA molecule which prevents translation of a target mRNA. Standard techniques are used for introducing siRNA into cells, including those wherein DNA is used as the template to transcribe RNA. The siRNA comprises a sense nucleic acid sequence and an antisense nucleic acid sequence of the polynucleotide encoding human B7330N protein (SEQ ID NO: 24 or 26). The siRNA is constructed such that a single transcript (double stranded RNA) has both the sense and complementary antisense sequences from the target gene, e.g., a hairpin.

Binding of the siRNA to a transcript corresponding to B7330N in the target cell results in a reduction in the protein production by the cell. The length of the oligonucleotide is at least 10 nucleotides and may be as long as the naturally-occurring the transcript. Preferably, the oligonucleotide is less than about 75, about 50, about 25 nucleotides in length. Most preferably, the oligonucleotide is about 19 to about 25 nucleotides in length. Examples of B7330N siRNA oligonucleotide which inhibit the growth of the cancer cell include the target sequence containing SEQ ID NOs: 18 or 22. Furthermore, in order to enhance the inhibition activity of the siRNA, nucleotide “u” can be added to 3' end of the antisense strand of the target sequence. The number of “u”s to be added is at least about 2, generally about 2 to about 10, preferably about 2 to about 5. The added “u”s form single strand at the 3' end of the antisense strand of the siRNA.

A B7330N siRNA is directly introduced into the cells in a form that is capable of binding to the mRNA transcripts. In these embodiments, the siRNA molecules of the invention are typically modified as described above for antisense molecules. Other modifications are also possible, for example, cholesterol-conjugated siRNAs have shown improved pharmacological properties (Song et al. *Nature Med.* 9:347-51 (2003)). Alternatively, the DNA encoding the B7330N siRNA is in a vector.

Vectors are produced for example by cloning a B7330N target sequence into an expression vector operatively-linked regulatory sequences flanking the B7330N sequence in a manner that allows for expression (by transcription of the DNA molecule) of both strands (Lee, N. S. et al., (2002) Nature Biotechnology 20: 500-5). An RNA molecule that is antisense to B7330N mRNA is transcribed by a first promoter (e.g., a promoter sequence 3' of the cloned DNA) and an RNA molecule that is the sense strand for the B7330N mRNA is transcribed by a second promoter (e.g., a promoter sequence 5' of the cloned DNA). The sense and antisense strands hybridize in vivo to generate siRNA constructs for silencing of the B7330N gene. Alternatively, two constructs are utilized to create the sense and antisense strands of a siRNA construct. Cloned B7330N can encode a construct having secondary structure, e.g., hairpins, wherein a single transcript has both the sense and complementary antisense sequences from the target gene.

Furthermore, a loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence that specifically hybridizes to an mRNA or a cDNA from a B7330N gene. In preferred embodiments, [A] is a ribonucleotide sequence corresponding a sequence of nucleotides 417-435 of SEQ ID NO: 24 or 623-641 of SEQ ID NO: 26 (SEQ ID NO: 18) and 1366-1384 of SEQ ID NO: 24 or 1572-1590 of SEQ ID NO: 26 (SEQ ID NO: 22),

[B] is a ribonucleotide sequence consisting of about 3 to about 23 nucleotides, and

[A'] is a ribonucleotide sequence consisting of the complementary sequence of [A]. The loop sequence may consist of arbitrary sequence having preferably 3 to 23 nucleotide in length. The loop sequence, for example, can be selected from group consisting of following sequences (world-wide-web.ambion.com/techlib/tb/tb.sub.--506.html). In the siRNA of the present invention, nucleotide “U” can be added to the 3' end of [A'], in order to enhance the inhibiting activity of the siRNA. The number of “u”s to be added is at least about 2, generally about 2 to about 10, preferably about 2 to about 5. Furthermore, loop sequence consisting of 23 nucleotides also provides active siRNA (Jacque, J. M., et al., (2002) Nature 418: 435-8).

CCC, CCACC or CCACACC: Jacque, J. M., et al., Nature, Vol. 418: 435-8 (2002);

UUCG: Lee, N. S., et al., (2002) Nature Biotechnology 20: 500-5; Fruscoloni, P., et al., Proc. Natl. Acad. Sci. USA 100 (4): 1639-44 (2003); and UUCAAGAGA: Dykxhoom, D. M., et al., Nature Reviews Molecular Cell Biology 4: 457-67 (2003).

For example, preferable siRNAs having hairpin structure of the present invention are shown below. In the following structure, the loop sequence can be selected from group consisting of CCC, UUCG, CCACC, CCACACC, and UUCAAGAGA. Preferable loop sequence is UUCAAGAGA (“ttcaagaga” in DNA).

gcacuguuucaaugccuuu-[B]-aaaggcauugaaacagugc (for target sequence of SEQ ID NO: 18)

gagaaauccuucggugaca-[B]-ugucaccgaaggauuucuc (for target sequence of SEQ ID NO: 22)

The regulatory sequences flanking the B7330N sequence are identical or are different, such that their expression can be modulated independently, or in a temporal or spatial manner. siRNAs are transcribed intracellularly by cloning the B7330N gene templates into a vector containing, e.g., a RNA polymerase III transcription unit from the small nuclear RNA (snRNA) U6 or the human H1 RNA promoter. For introducing the vector into the cell, transfection-enhancing agent can be used. FuGENE (Roche diagnostics), Lipofectamine 2000 (Invitrogen), Oligofectamine (Invitrogen), and Nucleofector (Wako pure Chemical) are useful as the transfection-enhancing agent.

The nucleotide sequence of siRNAs may be designed using an siRNA design computer program available from the Ambion website (world-wide-web.ambion.com/techlib/misc/siRNA_finder.html). Nucleotide sequences for the siRNA are selected by the computer program based on the following protocol:

Selection of siRNA Target Sites:

1. Beginning with the AUG start codon of the object transcript, scan downstream for AA dinucleotide sequences. Record the occurrence of each AA and the 3' adjacent 19 nucleotides as potential siRNA target sites. Tuschl, et al. Genes Dev 13(24): 3191-7 (1999), don't recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST (Altschul S F, et al., Nucleic Acids Res. 1997; 25(17):3389-402; J Mol. Biol. 1990; 215(3):403-10), which can be found on the NCBI server at: world-wide-web.ncbi.nhn.nih.gov/BLAST/.
3. Select qualifying target sequences for synthesis. At Ambion, preferably several target sequences can be selected along the length of the gene for evaluation.

Oligonucleotides and oligonucleotides complementary to various portions of B7330N mRNA were tested in vitro for their ability to decrease production of B7330N in tumor cells (e.g., using the HBL-100, HCC1937, MCF-7, MDA-MB-435s, YMB1, SKBR3, T47D, BT-20, BT-474, BT-549, HCC1143, HCC1500, HCC1599, MDA-MB-157, MDA-MB453, OUCB-F, ZR-75-1 breast cancer cell line) according to standard methods. A reduction in B7330N gene product in cells contacted with the candidate siRNA composition compared to cells cultured in the absence of the candidate composition is detected using B7330N-specific antibodies or other detection strategies. Sequences which decrease production of B7330N in in vitro cell-based or cell-free assays are then tested for there inhibitory effects on cell growth. Sequences which inhibit cell growth in in vitro cell-based assay are test in in vivo in rats or mice to confirm decreased B7330N production and decreased tumor cell growth in animals with malignant neoplasms.

Also included in the invention are double-stranded molecules that include the nucleic acid sequence of target sequences, for example, nucleotides 417-435 of SEQ ID NO: 24 or 623-641 of SEQ ID NO: 26 (SEQ ID NO: 18) and 1366-1384 of SEQ ID NO: 24 or 1572-1590 of SEQ ID NO: 26 (SEQ ID NO: 22). In the present invention, the double-stranded molecule comprising a sense strand and an antisense strand, wherein the sense strand comprises a ribonucleotide sequence corresponding to SEQ ID NOs: 18, or 22 and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing the B7330N gene, inhibits expression of said gene. In the present invention, when the isolated nucleic acid is RNA or derivatives thereof, base "t" should be replaced with "u" in the nucleotide sequences. As used herein, the term "complementary" refers to Watson-Crick or Hoogsteen base pairing between nucleotides units of a nucleic acid molecule, and the term "binding" means the physical or chemical interaction between two nucleic acids or compounds or associated nucleic acids or compounds or combinations thereof.

Complementary nucleic acid sequences hybridize under appropriate conditions to form stable duplexes containing few or no mismatches. Furthermore, the sense strand and antisense strand of the isolated nucleotide of the present invention, can form double stranded nucleotide or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches. The nucleic acid molecule is less than 4381 nucleotides (for SEQ ID NO: 24) or 4556 nucleotides (for SEQ ID NO: 26) in length. For example, the nucleic acid molecule is less than 500, 200, or 75 nucleotides in length. Also included in the invention is a vector containing one or more of the nucleic acids described herein, and a cell containing the vectors. The isolated nucleic acids of the present invention are useful for siRNA against B7330N or DNA encoding the siRNA. When the nucleic acids are used for siRNA or coding DNA thereof, the sense strand is preferably longer than about 19 nucleotides, and more preferably longer than about 21 nucleotides.

The antisense oligonucleotide or siRNA of the invention inhibit the expression of the polypeptide of the invention and is thereby useful for suppressing the biological activity of the polypeptide of the invention. Also, expression-inhibitors, comprising the antisense oligonucleotide or siRNA of the invention, are useful in the point that they can inhibit the biological activity of the polypeptide of the invention. Therefore, a composition comprising antisense oligonucleotide or siRNA of the present invention are useful in treating a breast cancer. Examples of B7330N siRNA oligonucleotide which inhibit the expression in mammalian cells include the target sequence containing SEQ ID NOs: 18 or 22. Furthermore, in order to enhance the inhibition activity of the siRNA, nucleotide "u" can be added to 3' end of the antisense strand of the target sequence. The number of "u"s to be added is at least about 2, generally about 2 to about 10, preferably about 2 to about 5. The added "u"s form single strand at the 3'end of the antisense strand of the siRNA.

Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as breast cancer.

Furthermore, the present invention provides ribozymes that inhibit the expression of the B7330N polypeptide of the present invention.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi et al., FEBS Lett 228: 225 (1988)) and hairpin type ribozymes (Buzayan, Nature 323: 349 (1986); Kikuchi and Sasaki, Nucleic Acids Res 19: 6751 (1991)) are included in the small ribozymes. Methods for designing and constructing ribozymes are known in the art (see Koizumi et al., FEBS Lett 228: 228 (1988); Koizumi et al., Nucleic Acids Res. 17: 7059 (1989); Kikuchi and Sasaki, Nucleic Acids Res 19: 6751 (1991)). Thus, ribozymes inhibiting the expression of the polypeptides of the present invention can also be constructed based on their sequence information (SEQ ID NO: 24 or 26) and these conventional methods.

Ribozymes against B7330N gene inhibit the expression of over-expressed B7330N protein and is thus useful for suppressing the biological activity of the protein. Therefore, the ribozymes are useful in treating or preventing breast cancer.

Diagnosing Breast Cancer

Moreover, the present invention provides a method for diagnosing cell proliferative disease such as breast cancer using the expression level of the genes of the present invention as a diagnostic marker. The present invention also provides a method for determining a predisposition to breast cancer in a subject by determining an expression level of the genes of the present invention in a patient-derived biological sample, such as tissue sample. An alteration, e.g., an increase in the level of expression of a gene as compared to a normal control level of the gene, indicates that the subject may suffer from or is at risk of developing breast cancer.

When used in the context of the present invention the term “predisposition to breast cancer” encompasses a state of a subject of being predisposed to, having a tendency, prevalence, inclination or susceptibility to breast cancer. Moreover, said term also encompasses that a subject is at a risk of acquiring breast cancer.

This diagnosing method comprises the steps of: (a) detecting the expression level of the B7330N gene of the present invention; and (b) relating an elevation of the expression level to breast cancer. Likewise, in the method for determining a predisposition to breast cancer the same steps as mentioned before are applied.

The expression levels of the B7330N gene in a biological sample can be estimated by quantifying mRNA corresponding to or protein encoded by the B7330N gene. Quantification methods for mRNA are known to those skilled in the art. For example, the levels of mRNAs corresponding to the B7330N gene can be estimated by Northern blotting or RT-PCR. Since the full-length nucleotide sequences of the B7330N genes are shown in SEQ ID NO: 24 or 26, anyone skilled in the art can design the nucleotide sequences for probes or primers to quantify the B7330N gene.

Also the expression level of the B7330N gene can be analyzed based on the activity or quantity of protein encoded by the gene. A method for determining the quantity of the B7330N protein is shown in below. For example, immunoassay methods are useful for the determination of the proteins in biological materials. Any biological materials can be used as the biological sample for the determination of the protein or it’s activity so long as the marker gene (B7330N gene) is expressed in the sample of a breast cancer patient. For example, breast duct epithelium can be mentioned as such biological sample. However, bodily fluids such as blood and urine may be also analyzed. On the other hand, a suitable method can be selected for the determination of the activity of a protein encoded by the B7330N gene according to the activity of a protein to be analyzed.

Expression levels of the B7330N gene in a biological sample are estimated and compared with those in a normal sample (e.g., a sample derived from a non-diseased subject). When such a comparison shows that the expression level of the target gene is higher than those in the normal sample, the subject is judged to be affected with breast cancer. The expression level of a B7330N gene in the biological sample(s) from a normal subject and subject to be diagnosed may be determined at the same time. Alternatively, normal ranges of the expression levels can be determined by a statistical method based on the results obtained by analyzing the expression level of the gene in samples previously collected from a control group. A result obtained by comparing the sample of a subject is compared with the normal range; when the result does not fall within the normal range, the subject is judged to be affected with or is at risk of developing breast cancer.

In the present invention, a diagnostic agent for diagnosing cell proliferative disease, such as breast cancer, is also provided. The diagnostic agent of the present invention comprises a compound that binds to a polynucleotide or a polypeptide of the present invention. Preferably, an oligonucleotide that hybridizes to the polynucleotide of the present invention or an antibody that binds to the polypeptide of the present invention may be used as such a compound. Alternatively, an aptamer such as a RNA, DNA or peptide aptamers may be used.

The present method of diagnosing breast cancer may be applied for assessing the efficacy of treatment of breast cancer in a subject. According to the method, a biological sample, such as a test cell population, is obtained from a subject undergoing treatment for breast cancer. The method for assessment can be conducted according to conventional methods of diagnosing breast cancer.

If desired, biological samples are obtained from the subject at various time points before, during or after the treatment. The expression level of B7330N gene, in the biological sample is then determined and compared to a control level derived, for example, from a reference cell population which includes cells whose state of breast cancer (i.e., cancerous cell or non-cancerous cell) is known. The control level is determined in a biological sample that has not been exposed to the treatment.

If the control level is derived from a biological sample which contains no cancerous cell, a similarity between the expression level in the subject-derived biological sample and the control level indicates that the treatment is efficacious. A difference between the expression level of the B7330N gene in the subject-derived biological sample and the control level indicates a less favorable clinical outcome or prognosis.

The term “efficacious” refers that the treatment leads to a reduction in the expression of a pathologically up-regulated gene (B7330N gene) or a decrease in size, prevalence or proliferating potential of breast cancer cells in a subject. When a treatment is applied prophylactically, “efficacious” indicates that the treatment retards or prevents occurrence of breast cancer The assessment of breast cancer can be made using standard clinical protocols. Furthermore, the efficaciousness of a treatment is determined in association with any known method for diagnosing or treating breast cancer.

Moreover, the present method of diagnosing breast cancer may also be applied for assessing the prognosis of a subject with breast cancer by comparing the expression level of B7330N gene in a patient-derived biological sample, such as test cell population, to a control level. Alternatively, the expression level of B7330N gene in a biological sample derived from patients may be measured over a spectrum of disease stages to assess the prognosis of the patient.

An increase in the expression level of B7330N gene compared to a normal control level indicates less favorable prognosis. A similarity in the expression level of B7330N gene compared to a normal control level indicates a more favorable prognosis for the patient.

Screening Compounds

Using the B7330N gene, proteins encoded by the gene or transcriptional regulatory region of the gene, compounds can be screened that alter the expression of the gene or the biological activity of a polypeptide encoded by the gene. Such compounds are used as pharmaceuticals for treating or preventing breast cancer.

Therefore, the present invention provides a method of screening for a compound for treating or preventing breast cancer using the polypeptide of the present invention. An embodiment of this screening method comprises the steps of: (a) contacting a test compound with a polypeptide of the present invention; (b) detecting the binding activity between the polypeptide of the present invention and the test compound; and (c) selecting the compound that binds to the polypeptide of the present invention. All embodiments described herein with respect to the polypeptide, polynucleotide, vectors and/or host cells of the present invention also pertain to the herein disclosed screening methods, miutatis mutandis, which apply said polypeptide, polynucleotide, vectors and/or host cells.

The polypeptide of the present invention to be used for screening may be a recombinant polypeptide or a protein derived from the nature or a partial peptide thereof. The polypeptide of the present invention to be contacted with a test compound can be, for example, a purified polypeptide, a soluble protein, a form bound to a carrier or a fusion protein fused with other polypeptides.

As a method of screening for proteins, for example, that bind to the polypeptide of the present invention using the polypeptide of the present invention, many methods well known by a person skilled in the art can be used. Such a screening can be conducted by, for example, immunoprecipitation method, specifically, in the following manner. The gene encoding the polypeptide of the present invention is expressed in host (e.g., animal) cells and so on by inserting the gene to an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-α promoter (Kim et al., Gene 91: 217-23 (1990)), the CAG promoter (Niwa et al., Gene 108: 193 (1991)), the RSV LTR promoter (Cullen, Methods in Enzymology 152: 684-704 (1987)) the SRα promoter (Takebe et al., Mol Cell Biol 8: 466 (1988)), the CMV immediate early promoter (Seed and Arnffo, Proc Natl Acad Sci USA 84: 3365-9 (1987)), the SV40 late promoter (Gheysen and Fiers, J Mol Appl Genet. 1: 385-94 (1982)), the Adenovirus late promoter (Kaufman et al., Mol Cell Biol 9: 946 (1989)), the HSV TK promoter and so on. The introduction of the gene into host cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1641-3 (1984)), the Lipofectin method (Derijard B, Cell 76: 1025-37 (1994); Lamb et al., Nature Genetics 5: 22-30 (1993): Rabindran et al., Science 259: 230-4 (1993)) and so on. The polypeptide of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP) and so on by the use of its multiple cloning sites are commercially-available.

A fusion protein prepared by introducing only small epitopes consisting of several to a dozen amino acids so as not to change the property of the polypeptide of the present invention by the fusion is also reported. Epitopes, such as polyhistidine (Mis-tag), influenza aggregate HA, human c-myc, FLAG Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the polypeptide of the present invention (Experimental Medicine 13: 85-90 (1995)).

In immunoprecipitation, an immune complex is formed by adding these antibodies to cell lysate prepared using an appropriate detergent. The immune complex consists of the polypeptide of the present invention, a polypeptide comprising the binding ability with the polypeptide, and an antibody. Immunoprecipitation can be also conducted using antibodies against the polypeptide of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide of the present invention, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide of the present invention is difficult to detect by a common staining method, such as Coomassie staining or silver staining, the detection sensitivity for the protein can be improved by culturing cells in culture medium containing radioactive isotope, $^{35}S$-methionine or $^{35}S$-cysteine, labeling proteins in the cells, and detecting the proteins. The target protein can be purified directly from the SDS-polyacrylamide gel and its sequence can be determined, when the molecular weight of a protein has been revealed.

As a method for screening proteins binding to the polypeptide of the present invention using the polypeptide, for example, West-Western blotting analysis (Skolnik et al., Cell 65: 83-90 (1991)) can be used. Specifically, a protein binding to the polypeptide of the present invention can be obtained by preparing a cDNA library from cells, tissues, organs (for example, tissues such as breast cancer cell lines and normal human placenta, pancreas, stomach, trachea, mammary gland and bone marrow), or cultured cells (e.g., HBC4, HBC5, MCF-7, MDA-MB-231, YMB1, SKBR3, T47D) expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide of the invention may be labeled by utilizing the binding between biotin and avidin, or by utilizing an antibody that specifically binds to the polypeptide of the present invention, or a peptide or polypeptide (for example, GST) that is fused to the polypeptide of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene and such can be used in addition to the HIS3 gene.

A compound binding to the polypeptide of the present invention can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized polypeptide of the present invention is exposed to synthetic chemical compounds, or natural substance banks or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the protein of the present invention (including agonist and antagonist) are well known to one skilled in the art.

Alternatively, the present invention provides a method of screening for a compound for treating or preventing breast cancer using the polypeptide of the present invention comprising the steps as follows:

(a) contacting a test compound with the polypeptide of the present invention;

(b) detecting the biological activity of the polypeptide of step (a); and (c) selecting a compound that suppresses the biological activity of the polypeptide in comparison with the biological activity detected in the absence of the test compound.

Since the B7330N protein of the present invention have the activity of promoting cell proliferation of breast cancer cells, a compound which inhibits this activity of this protein of the present invention can be screened using this activity as an index.

Any polypeptides can be used for screening so long as they comprise the biological activity of the B7330N protein. Such biological activity includes cell-proliferating activity of the human B7330N protein. For example, a human B7330N protein can be used and polypeptides functionally equivalent to these proteins can also be used. Such polypeptides may be expressed endogenously or exogenously by cells.

Figure 3:
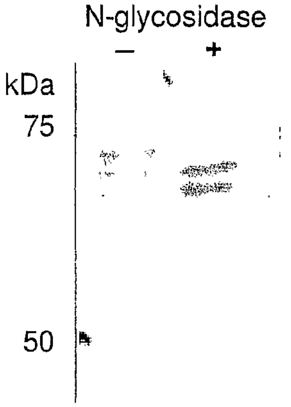
FIG. 3(*a*) shows treatment of N-glycosydase to B7330N protein.
Figure 3:
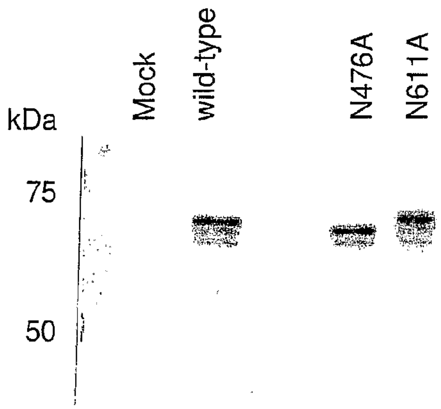
Figure 3:
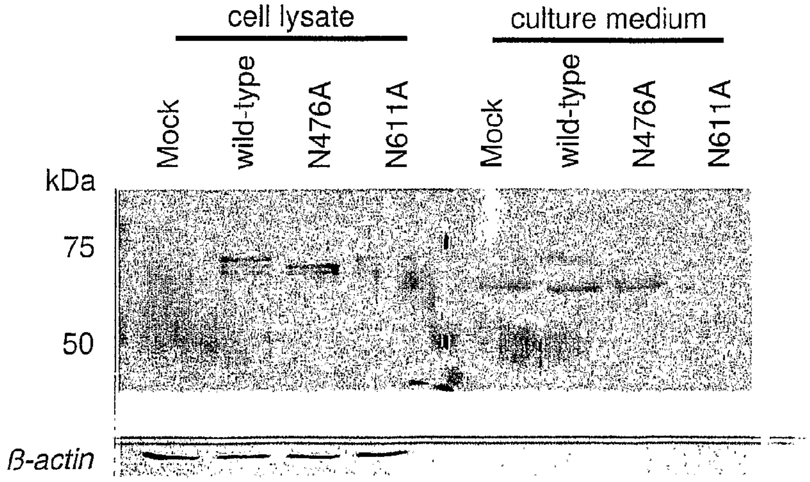
Figure 5:
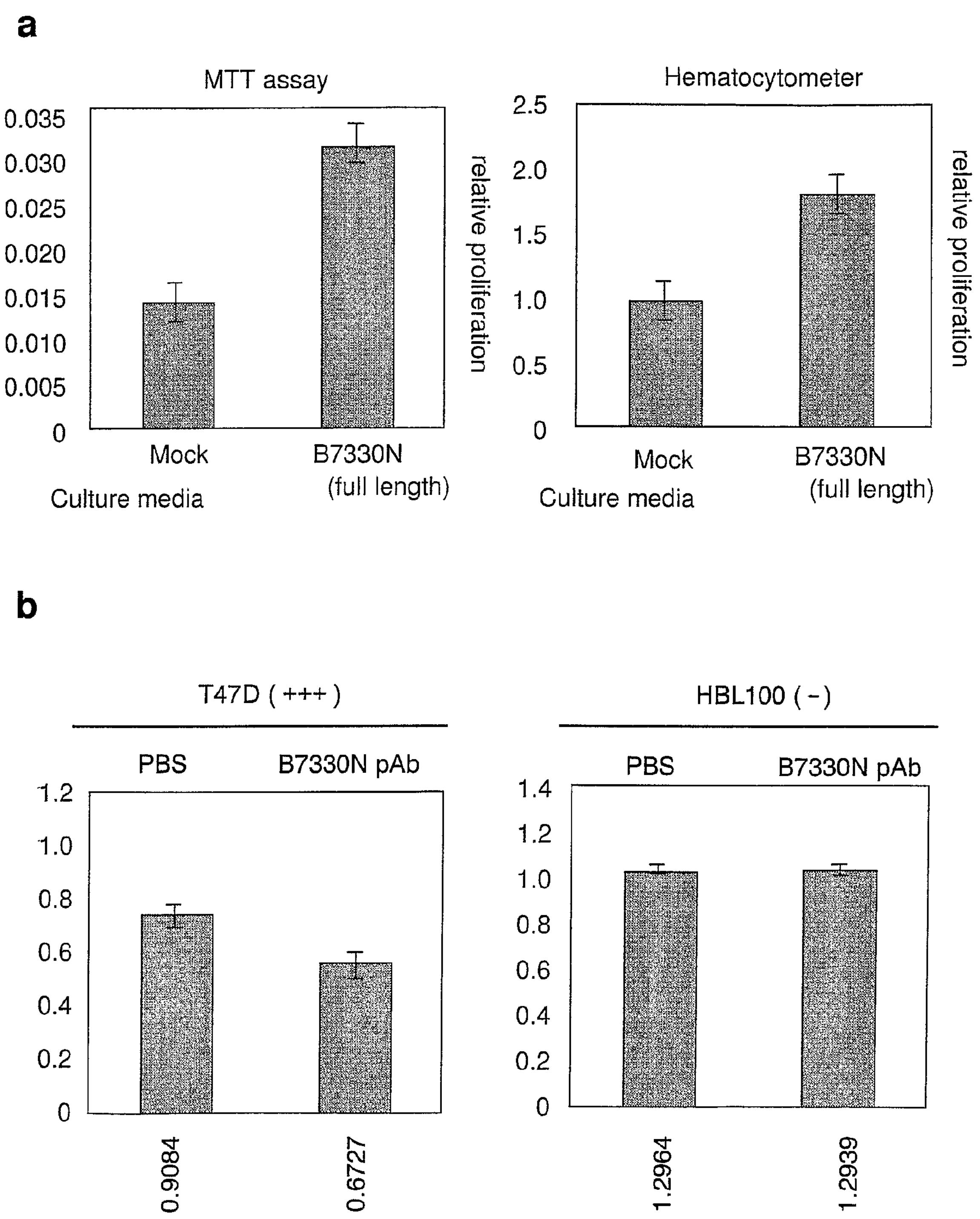
FIG. 5 shows detection of an autocrine effect of B7330N. a, COS7 cultures in medium containing B7330N showed enhancement of cell growth compared to COS7 cells in medium without B7330N. b, Impairment of breast cancer-cell growth after exposure to anti-B7330N pAb. Cells were exposed for 5 days to pre-immune rabbit IgG or anti-HIG2 pAb, at concentrations of 10.2 μg/mL. The histogram shows average values from three experiments, ±SD.
Figure 8:
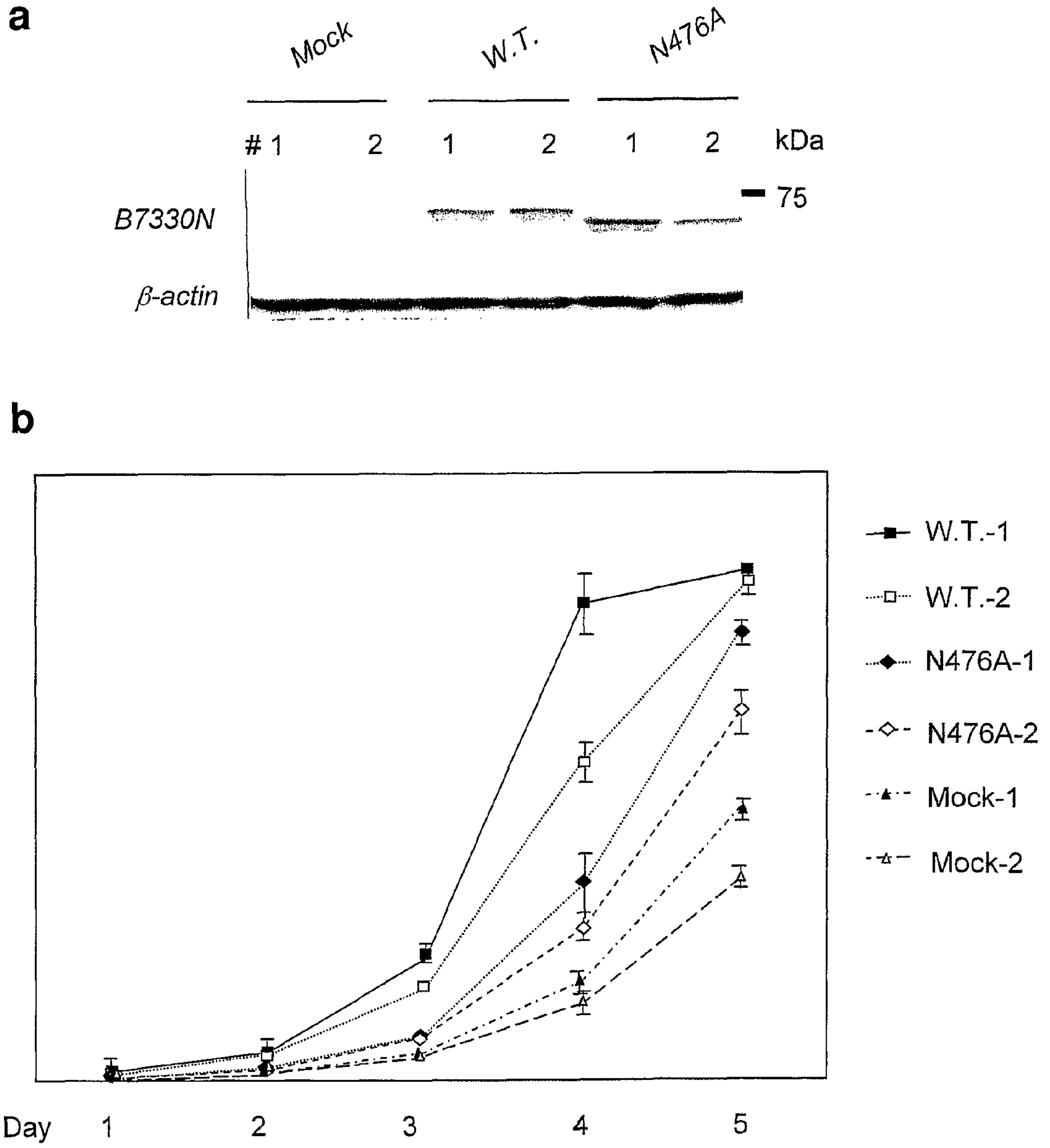
FIG. 8. Growth-promoting effect of exogenous B7330N in NIH3T3 cells. a, Western blot analysis of cells expressing exogenous B7330N at high level or those transfected with mock vector. Exogenous introduction of B7330N expression were validated with anti-HA-tag monoclonal antibody. Beta-actin served as a loading control. b, in vitro growth of NIH3T3-B7330N cells. NIH3T3 cells transfected with WT-B7330N (WT-B7330N-#1, and -#2) and mock (NIH3T3-Mock-#1 and -#2), as measured by MTT assay.

The present invention is based in part on the discovery of a novel glycosylation of B7330N protein, which is involved in proliferation of cancer cells, as detailed below. B7330 plays a role in autocrine regulation of cell growth through the activation of signal transduction for cell proliferation (FIG. 5*a*, 5*b*). In N476A mutant which was replaced 476N (asparagine) with A (alanine), no glycosylation was observed (FIG. 3*b*). Exogenous wild-type B7330N was secreted into culture medium, whereas the N476A protein was not detected in culture medium, suggesting glycosylation on Asn-476 of B7330N protein is necessary for secretion (FIG. 3*c*). Further, cells expressing wild type of B7330N grew much faster than cells transfected with N476A (FIG. 8*b*). Accordingly, cell growth of breast cancer may be supressed by inhibition of the glycosylation of B7330N.

The invention thus provides a method of screening for a compound for treating or preventing breast cancer that modulates glycosylation level of B7330N comprising the steps as follows:

(a) contacting a test compound with a cell expressing B7330N polypeptide or functional equivalent thereof;

(b) detecting the glycosylation level of the polypeptide; and (c) selecting a compound that suppresses the glycosylation level of the polypeptide in comparison with the glycosylation level detected in the absence of the test compound.

Alternatively, the present invention provides a method of screening for a compound for treating or preventing breast cancer using the polypeptide of the present invention comprising the steps as follows:

a) contacting a test compound with B7330N polypeptide or partial polypeptide comprising glycosylation site of the B7330N polypeptide, under the condition capable of glycoslation of the peptide;

(b) detecting the glycosylation level of the polypeptide; and (c) selecting a compound that suppresses the glycosylation level of the polypeptide in comparison with the glycosylation level detected in the absence of the test compound.

In a preferred aspect of the aforementioned methods of screening for a compound for treating or preventing breast cancer comprising, inter alia, the detection of the glycosylation level of the polypeptide of the present invention, said glycosylation level is that of asparagines 476 of the polypeptide of the present invention, in particular it is the glycosylation level of asparagine 476 of the amino acid sequence of SEQ ID NO: 25 or a homologous portion thereof. As described above, the skilled person is readily in a position to determine in a polypeptide of the present invention the position corresponding to position 476 of the amino acid sequence of SEQ ID NO: 25.

These methods are practiced by contacting a cell expressing B7330N polypeptide or functional equivalent thereof having glycosylation site, or a polypeptide itself with one or more candidate compounds, and detecting glycosylation level of the contacted B7330N or the functional equivalent.

A compound that modulates glycosylation level of the B7330N or functional equivalent is thereby identified.

In the present invention, the term "functionally equivalent" also means that the subject protein has the same or substantially the same glycosylation level as B7330N. In particular, the protein or a partial amino acid of the protein which includes glycosylation site are catalyzed the glycosylation. Whether a subject protein has the target activity can be determined by the present invention. Namely, the glycosylation level of the B7330N protein can be detected by contacting a polypeptide with a test compound under conditions suitable for glycosylation of the protein.

In the present invention, glycosylation level of a B7330N polypeptide can be determined by methods known in the art. For example, glycosylation of the polypeptide may be detected by comparing the molecular weight. Molecular weight of a glycosylated protein is larger than that of predicted size calculated from the amino acid sequence of the polypeptide by addition of glycoside chain. Furthermore, when the molecular weight of glycosylated protein might be reduced by glycosidase treatment, it was confirmed that the difference of the molecular is caused by addition of glycoside chain. Methods for estimating a molecular weight of a protein are well known.

Alternatively, radiolabeled donor for glycosylation may be used for detection the addition of glycoside chain to the polypeptide. Transfer of the radiolabel to the B7330N protein can be detected, for example, by SDS-PAGE electrophoresis and fluorography. Alternatively, following the reaction the B7330N peptides can be separated from the glycosyl donor by filtration, and the amount of radiolabel retained on the filter quantitated by scintillation counting. Other suitable labels that can be attached to glycosyl donor, such as chromogenic and fluorescent labels, and methods of detecting transfer of these labels to the B7330N protein, are known in the art. Alternatively, glycosylation level of B7330N can be determined reagents that selectively recognize glycosylated level of the polypeptide. For example, after incubation of the B7330N polypeptide and candidate compound, under the condition capable of glycosylation of the polypeptide, the glycosylation level of the polypeptide can be detected by immunological method. Any immunological techniques using an antibody recognizing glycosylated polypeptide can be used for the detection. For example, an antibody against glycosylated polypeptide is commercial available. ELISA or Immunoblotting with antibodies recognizing glycosylated polypeptide can be used for the present invention.

Instead of using antibodies, glycosylated protein can be detected using reagents that selectively bind glycoside chain with high affinity. Such reagents are known in the art or can be determined by screening assays known in the art. For example, lectins are well known as glycoside chain specific probe. Lectin reagent conjugated with detectable label such as alkaline-phosphatase is also commercially available.

Glycosylation level of polypeptide in a cell may be estimated by separation of cell lysate. For example, SDS-polyacrylamide gel can be used as the separation of the polypeptide. The polypeptide separated in the gels is transferred to nitrocellulose membranes for immunoblotting analysys.

The compound isolated by this screening is a candidate for agonists or antagonists of the polypeptide of the present invention. The term "agonist" refers to molecules that activate the function of the polypeptide of the present invention by binding thereto. Likewise, the term "antagonist" refers to molecules that inhibit the function of the polypeptide of the present invention by binding thereto. Moreover, a compound isolated by this screening is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity as described in the Examples.

In a further embodiment, the present invention provides methods for screening compounds for treating or preventing breast cancer. As discussed in detail above, by controlling the expression levels of the B7330N, one can control the onset and progression of breast cancer. Thus, compounds that may be used in the treatment or prevention of breast cancer can be identified through screenings that use the expression levels of B7330N as indices. In the context of the present invention, such screening may comprise, for example, the following steps:

a) contacting a test compound with a cell expressing the B7330N; and b) selecting a compound that reduces the expression level of B7330N in comparison with the expression level detected in the absence of the test compound.

Cells expressing at least one of the B7330N include, for example, cell lines established from breast cancers; such cells can be used for the above screening of the present invention (e.g., HBC4, HBC5, MCF-7, MDA-MB-231, YMB1, SKBR3, T47D, BT-20, HCC1500 or MDA-MB-453. etc.). The expression level can be estimated by methods well known to one skilled in the art. In the method of screening, a compound that reduces the expression level of B7330N can be selected as candidate agents to be used for the treatment or prevention of breast cancer.

Alternatively, the screening method of the present invention may comprise the following steps:

a) contacting a test compound with a cell into which a vector comprising the transcriptional regulatory region of a marker gene and a reporter gene that is expressed under the control of the transcriptional regulatory region has been introduced, wherein the marker gene is B7330N, b) measuring the expression level or activity of said reporter gene; and c) selecting a compound that reduces the expression level or activity of said reporter gene as compared to a control level detected in the absence of the test compound.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia).

Alternatively, B7330N polypeptide may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances such as radioisotope (e.g., $^{3}H$, $^{14}C$, $^{32}P$, $^{33}P$, $^{35}S$, $^{125}I$, $^{131}I$), enzymes (e.g., alkaline phosphatase, horseradish peroxidase, β-galactosidase, β-glucosidase), fluorescent substances (e.g., fluorescein isothiosyanete (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

In case of using an antibody in the present screening, the antibody is preferably labeled with one of the labeling substances mentioned above, and detected or measured based on the labeling substance. Alternatively, the antibody against the B7330N polypeptide or actin may be used as a primary antibody to be detected with a secondary antibody that is labeled with a labeling substance. Furthermore, the antibody bound to the protein in the screening of the present invention may be detected or measured using protein G or protein A column.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art (DeWitt et al. (1993) Proc. Natl. Acad. Sci. USA 90: 6909; Erb et al. (1994) Proc. Natl. Acad. Sci. USA 91: 11422; Zuckermann et al. (1994) J. Med. Chem. 37: 2678; Cho et al. (1993) Science 261: 1303; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233). Libraries of compounds may be presented in solution (see Houghten (1992) Bio/Techniques 13: 412) or on beads (Lam (1991) Nature 354: 82), chips (Fodor (1993) Nature 364: 555), bacteria (U.S. Pat. No. 5,223,409), spores (U.S. Pat. Nos. 5,571,698; 5,403,484, and 5,223,409), plasmids (Cull et al. (1992) Proc. Natl. Acad. Sci. USA 89: 1865) or phage (Scott and Smith (1990) Science 249: 386; Devlin (1990) Science 249: 404; Cwirla et al. (1990) Proc. Natl. Acad. Sci. USA 87: 6378; Felici (1991) J. Mol. Biol. 222: 301; US Pat. Application 2002103360).

A compound isolated by the screening methods of the present invention is a candidate for drugs which inhibit the activity of the polypeptide of the present invention, for treating or preventing diseases attributed to, for example, cell proliferative diseases, such as breast cancer. A compound in which a part of the structure of the compound obtained by the present screening methods of the present invention is converted by addition, deletion and/or replacement, is included in the compounds obtained by the screening methods of the present invention.

Pharmaceutical Compositions for Treating or Preventing Breast Cancer

The present invention provides compositions for treating or preventing breast cancer comprising any of the compounds selected by the screening methods of the present invention.

When administrating a compound isolated by the screening methods of the present invention as a pharmaceutical for humans or other mammals, such as mice, rats, guinea-pigs, rabbits, cats, dogs, sheep, pigs, cattle, monkeys, baboons, chimpanzees, for treating a cell proliferative disease (e.g., breast cancer) the isolated compound can be directly administered or can be formulated into a dosage form using known pharmaceutical preparation methods. For example, according to the need, the drugs can be taken orally, as sugarcoated tablets, capsules, elixirs and microcapsules; or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections and also as intranasal, intramuscular or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Furthermore, the present invention provides pharmaceutical compositions for treating or preventing breast cancer comprising active ingredients that inhibits the expression of B7330N gene. Such active ingredients include antisense polynucleotides, siRNAs or ribozymes against the B7330N gene or derivatives, such as expression vector, of the antisense polynucleotides, siRNAs or ribozymes.

These active ingredients can be made into an external preparation, such as a liniment or a poultice, by mixing with a suitable base material which is inactive against the derivatives. Also, as needed, they can be formulated into tablets, powders, granules, capsules, liposome capsules, injections, solutions, nose-drops and freeze-drying agents by adding excipients, isotonic agents, solubilizers, stabilizers, preservatives, pain-killers and such. These can be prepared according to conventional methods.

The active ingredient is given to the patient by directly applying onto the ailing site or by injecting into a blood vessel so that it will reach the site of ailment. A mounting medium can also be used to increase durability and membrane-permeability. Examples of mounting medium include liposome, poly-L-lysine, lipid, cholesterol, lipofectine or derivatives of these.

The dosage of such compositions of the present invention can be adjusted suitably according to the patient's condition and used in desired amounts. For example, a dose range of 0.1 to 100 mg/kg, preferably 0.1 to 50 mg/kg can be administered.

Another embodiment of the present invention is a composition for treating or preventing breast cancer comprising an antibody against a polypeptide encoded by the B7330N gene or fragments of the antibody that bind to the polypeptide.

Although there are some differences according to the symptoms, the dose of an antibody or fragments thereof for treating or preventing breast cancer is about 0.11 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the condition of the patient, symptoms of the disease and method of administration, it is convenient to intravenously inject a dose of about 0.01 mg to about 30 mg per day, preferably about 0.1 to about 20 mg per day and more preferably about 0.1 to about 10 mg per day. Also in the case of other animals too, it is possible to administer an amount converted to 60 kg of body-weight.

Methods for Treating or Preventing Breast Cancer

The invention provides a method for treating or preventing breast cancer in a subject. Therapeutic compounds are administered prophylactically or therapeutically to subject suffering from or at risk of (or susceptible to) developing breast cancer. Such subjects are identified using standard clinical methods or by detecting an aberrant expression level or activity of B7330N. Prophylactic administration occurs prior to the manifestation of overt clinical symptoms of disease, such that a disease or disorder is prevented or, alternatively, delayed in its progression.

The therapeutic method includes decreasing the expression or function of B7330N gene. In these methods, the subject is treated with an effective amount of a compound, which decreases the over-expressed gene (B7330N gene) in the subject. Administration can be systemic or local. Therapeutic compounds include compounds that decrease the expression level of such gene endogenously existing in the breast cancerous cells (i.e., compounds that down-regulate the expression of the over-expressed gene). Administration of such therapeutic compounds counter the effects of aberrantly-over expressed gene in the subject's cells and are expected to improve the clinical condition of the subject. Such compounds can be obtained by the screening method of the present invention described above.

The expression of B7330N gene may be also inhibited in any of several ways known in the art including administering to the subject a nucleic acid that inhibits or antagonizes the expression of the gene. Antisense oligonucleotides, siRNA or ribozymes which disrupts expression of the gene can be used for inhibiting the expression of the gene. Antisense oligonucleotides, siRNA or ribozymes which can be used for inhibiting the expression of B7330N gene are described herein above.

As noted above, antisense-oligonucleotides corresponding to the nucleotide sequence of B7330N gene can be used to reduce the expression level of the B7330N gene. Specifically, the antisense-oligonucleotides of the present invention may act by binding to any of the polypeptides encoded by the B7330N gene, or mRNAs corresponding thereto, thereby inhibiting the transcription or translation of the gene, promoting the degradation of the mRNAs, and/or inhibiting the expression of proteins encoded by the gene, and finally inhibiting the function of the B7330N proteins.

An antisense-oligonucleotides and derivatives thereof can be made into an external preparation, such as a liniment or a poultice, by mixing with a suitable base material which is inactive against the derivative and used in the method for treating or preventing breast cancer of the present invention.

The nucleic acids that inhibit a gene product of over-expressed gene also include small interfering RNAs (siRNA) comprising a combination of a sense strand nucleic acid and an antisense strand nucleic acid of the nucleotide sequence encoding the B7330N gene. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, e.g., a hairpin.

The method is used to suppress gene expression of a cell with up-regulated expression of the B7330N gene. Binding of the siRNA to the B7330N gene transcript in the target cell results in a reduction of B7330N protein production by the cell.

The nucleic acids that inhibit a gene product of over-expressed gene also include ribozymes against the over-expressed gene (B7330N gene).

Moreover, the present invention provides a method for treating or preventing a cell proliferative disease, such as breast cancer, using an antibody against the polypeptide of the present invention. According to the method, a pharmaceutically effective amount of an antibody against the polypeptide of the present invention is administered. Since the expression of the B7330N protein are up-regulated in breast cancer cells and the suppression of the expression of these proteins leads to the decrease in cell proliferating activity, it is expected that cell proliferative diseases can be treated or prevented by binding the antibody and these proteins. Thus, an antibody against the polypeptide of the present invention is administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day.

Alternatively, an antibody binding to a cell surface marker specific for tumor cells can be used as a tool for drug delivery. For example, the antibody conjugated with a cytotoxic agent is administered at a dosage sufficient to injure tumor cells.

Another aspect of the present invention is a method for treating or preventing breast cancer, said method comprising the step of administering a pharmaceutically effective amount of the agent which inhibits the glycosylation of asparagine 476 of an amino acid sequence of a polypeptide of the present invention, in particular of the amino acid sequence of a polypeptide of SEQ ID NO: 25.

The present invention also relates to a method of inducing anti-tumor immunity comprising the step of administering B7330N protein or an immunologically active fragment thereof, or a polynucleotide encoding the protein or fragments thereof. The B7330N protein or the immunologically active fragments thereof are useful as vaccines against cell proliferative diseases such as breast cancer. In some cases the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, vaccine against cell proliferative disease refers to a substance that has the function to induce anti-tumor immunity upon inoculation into animals. In general, anti-tumor immunity includes immune responses such as follows:

induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DC, peripheral blood mononuclear cells (PBMCs) may also be used as the APC. The induction of CTL is reported that it can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide and when growth of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of cell proliferating diseases, such as breast cancers. Therapy against cancer or prevention of the onset of cancer includes any of the steps, such as inhibition of the growth of cancerous cells, involution of cancer and suppression of occurrence of cancer. Decrease in mortality of individuals having cancer, decrease of tumor markers in the blood, alleviation of detectable symptoms accompanying cancer and such are also included as the effect of therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test or ANOVA may be used for statistical analysis.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum and such, but are not limited thereto. Furthermore, the vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, tumors can be treated or prevented, for example, by the ex vivo method. More specifically, PBMCs of a subject receiving treatment or prevention therapy are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing a cell proliferative disease, such as breast cancer, comprising a pharmaceutically effective amount of the B7330N polypeptide is provided. The pharmaceutical composition may be used for raising anti tumor immunity. The normal expression of B7330N is restricted to placenta, pancreas, stomach, trachea, mammary gland and bone marrow. Therefore, suppression of this gene may not adversely affect other organs. Thus, the B7330N polypeptides are preferable for treating cell proliferative disease, especially breast cancers. Furthermore, since peptide fragments of proteins specifically expressed in cancerous cells were revealed to induce immune response against the cancer, peptide fragments of B7330N can also be used in a pharmaceutical composition for treating or preventing cell proliferative diseases such as breast cancers. In the present invention, the polypeptide or fragment thereof is administered at a dosage sufficient to induce anti-tumor immunity, which is in the range of 0.1 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

In addition, polynucleotides encoding B7330N, or fragments thereof may be used for raising anti tumor immunity. Such polynucleotides may be incorporated in an expression vector to express B7330N, or fragments thereof in a subject to be treated. Thus, the present invention encompasses method for inducing anti tumor immunity wherein the polynucleotides encoding B7330N, or fragments thereof are administered to a subject suffering or being at risk of developing cell proliferative diseases such as breast cancer.

Of course, the herein described embodiments for methods of treatment or prevention of breast cancer or methods of inducing an anti tumor immunity, in particular anti breast tumor immunity apply, mutatis mutandis, to the uses of any of the compounds which are applied in said methods of treatment or prevention of breast cancer or said methods of inducing an anti tumor immunity as described herein for the preparation of a pharmaceutical composition for treating or preventing breast cancer or for inducing an anti tumor immunity, in particular anti breast tumor immunity in a subject.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference. Nothing herein is to be construed as an admission that the invention is not entitled to antedate such disclosure by virtue of prior invention.

BEST MODE FOR CARRYING OUT THE INVENTION

The present invention is illustrated in details by following Examples, but is not restricted to these Examples.

Materials and Methods

Breast Cancer Cell Lines and Tumor Specimens

Human-breast cancer cell lines HBL-100, HCC1937, MCF-7, MDA-MB-435s, YMB1, SKBR3, T47D, BT-20, BT-474, BT-549, HCC1143, HCC1500, HCC1599, MDA-MB-157, MDA-MB453, OUCB-F, ZR-75-1 and COS-7 cell lines are purchased from American Type Culture Collection (ATCC) and are cultured under their respective depositors' recommendation. HBC4, HBC5 and MDA-MB-231 cells lines are kind gifts from Dr. Yamori of Molecular Pharmacology, Cancer Chemotherapy Centre of the Japanese Foundation for Cancer Research. All cells were cultured in appropriate media; i.e. RPMI-1640 (Sigma, St. Louis, Mo.) for HBC4, HBC5, T47D, YMB1, OUCB-F, ZR-75-1, BT-549, HCC1143, HCC1500, HCC1599 and HCC1937 (with 2 mM L-glutamine); Dulbecco's modified Eagle's medium (Invitrogen, Carlsbad, Calif.) for BT474, HBL100, COS7; EMEM (Sigma) with 0.1 mM essential amino acid (Roche), 1 mM sodium pyruvate (Roche), 0.01 mg/ml Insulin (Sigma) for BT-20 and MCF-7; McCoy (Sigma) for SKBR3 (with 1.5 mM L-glutamine); L-15 (Roche) for MDA-MB-231, MDA-MB-157, MDA-MB453 and MDA-MB-435s. Each medium was supplemented with 10% fetal bovine serum (Cansera) and 1% antibiotic/antimycotic solution (Sigma). MDA-MB-231 and MDA-MB-435s cells were maintained at 37° C. an atmosphere of humidified air without $CO_2$. Other cell lines were maintained at 37° C. an atmosphere of humidified air with 5% $CO_2$. Clinical samples (breast cancer and normal breast duct) were obtained from surgical specimens, concerning which all patients had given informed consent.

Isolation of a Novel Human Gene Represented by spot B7330N on our cDNA Microarray Fabrication of the cDNA microarray slides has been described elsewhere (Ono K, et al., (2000) Cancer Res., 60, 5007-11). For each analysis of expression profiles we prepared duplicate sets of slides containing 27,648 cDNA spots, to reduce experimental fluctuation. Briefly, total RNAs were purified from each sample of laser-microdissected cells, and T7-based RNA amplification was carried out to obtain adequate quantities of RNA for microarray experiments. Aliquots of amplified RNA from breast cancer cells and the normal breast ductal cells were labeled by reverse transcription with Cy5-dCTP and Cy3-dCTP, respectively (Amersham Biosciences, Buckinghamshire, UK). Hybridization, washing, and detection were carried out as described previously (Ono K, et al., (2000) Cancer Res., 60, 5007-11). To detect genes that were commonly up-regulated in breast cancer, the overall expression patterns of the 27,648 genes on the microarray were screened to select those with expression ratios >3.0 that were present in >50% of i) all of 77 premenopausal breast cancer cases, ii) 69 invasive ductal carcinomas, iii) 31 well-, iv) 14 moderately-, or v) 24 poorly-differentiated lesions, respectively. Among the total of 493 genes that appeared to up-regulated in tumor cells, we focused on one with in-house identification number, B7330N because its expression ratio was greater than 3.0 in more than 30% of the informative breast cancer cases.

Semi-Quantitative RT-PCR Analysis

We extracted total RNA from each population of laser-captured cells and then performed T7-based amplification and reverse transcription as described previously (Kitahara O, et al., (2001) Cancer Res., 61, 3544-9). We prepared appropriate dilutions of each single-stranded cDNA for subsequent PCR by monitoring the glyceraldehyde-3-phosphate dehydrogenase (GAPDB) as a quantitative internal control. The PCR primer sequences were 5'-CGACCACTTTGTCAAGCTCA-3' (SEQ ID NO; 1) and 5'-GGTTGAGCACAGGGTACTTTATT-3' (SEQ ID NO; 2) for GAPDH; and 5'-GAGTCCAGGTAAGTGAATCTGTCC-3' (SEQ ID NO; 3) and 5'-ATTTCCACCGAGACCTCTCATC-3' (SEQ ID NO; 4) for B7330N.

Northern-Blot Analysis

Total RNAs were extracted from all breast cancer cell lines using RNeasy kit (QIAGEN) according to the manufacturer's instructions. After treatment with DNase I (Nippon Gene, Osaka, Japan), mRNA was isolated with mRNA purification kit (Amersham Biosciences) following the manufacturer's instructions. A 1-μg aliquot of each mRNA, along with polyA (+) RNAs isolated from normal adult human breast (BioChain), lung, heart, liver, kidney, bone marrow (BD, Clontech, Palo Alto, Calif.), were separated on 1% denaturing agarose gels and transferred to nylon membranes (Breast cancer-Northern blots). Breast cancer- and Human multiple-tissue Northern blots (Clontech, Palo Alto, Calif.) were hybridized with an [$\alpha^{32}$P]-dCTP-labeled PCR products of B7330N prepared by RT-PCR (see below). Pre-hybridization, hybridization and washing were performed according to the supplier's recommendations. The blots were autoradiographed with intensifying screens at −80° C. for 14 days. Specific probes for B7330N (502 bp) was prepared by RT-PCR using the following primer set; 5'-GAGTCCAGGTAAGTGAATCTGTCC-3' (SEQ ID NO; 3) and 5'-ATTTCCACCGAGACCTCTCATC-3' (SEQ ID NO; 4) and is radioactively labeled with megaprime DNA labeling system (Amersham Bioscience).

Construction of B7330N Expression Vectors

For constructing of B7330N expression vectors, the entire coding sequence of B7330N cDNA was amplified by the PCR using KOD-Plus DNA polymerase (Toyobo, Osaka, Japan) and the following primers; forward, 5'-CG<u>GAATTCA</u>TGAGGCTCCTCCGCAG-3' (SEQ ID NO; 5), (underline indicates EcoR I site), reverse, 5'-CCG<u>CTCGAG</u>GACAAAGAGCCACAACTGATG-3' (SEQ ID NO; 6) (underline indicates Xho I site). The PCR products were inserted into the EcoR I and Xho I sites of pCAGGS-HA expression vector. To make constructs of B7330N mutants, we substituted two asparagines residues (Asn-476 and Asn-611) which was predicted potential N-glycosylation sites in B7330N protein with alanine residues by using PCR site-direct mutagenesis kit (Invitrogen) and the following primers; N476A-F, 5'-ACAACTGCACTGTCACGCCTTTTCCTGGTACCTGC-3' (SEQ ID NO; 7) and N476A-R, 5'-GCAGGTACCAGGAAAAGGCGTGACAGTGCAGTTGT-3' (SEQ ID NO; 8); N611A-F, 5'-CATGGCCCCCTGCGCACCCAGTGACCCCC-3' (SEQ ID NO; 9) and N611A-R, 5'-GGGGGTCACTGGGTGCGCAGGGGGCCATG-3' (SEQ ID NO; 10). These constructs (pCAGGS-B7330N-HA, pCAGGS-N476A-HA and pCAGGS-N611A-HA) were confirmed by DNA sequencing. To make a construction for dimerization experiments, entire coding sequence of B7330N was cloned into pcDNA3.1-myc-his vector (Invitrogen).

Immunocytochemical Staining

To initially examine the sub-cellular localization of exogenous B7330N, we seeded COS7 cells at $1\times10^5$ per well for exogenous expression. After 72 hours, we transiently transfected with 1 μg of pCAGGS-B7330N-HA into COS7 cells using FuGENE 6 transfection reagent (Roche) according to the manufacturer's instructions, respectively. Then, cells were fixed with PBS containing 4% paraformaldehyde for 15 min, and rendered permeable with PBS containing 0.1% Triton X-100 for 2.5 min at 4° C. Subsequently the cells were covered with 3% BSA in PBS for 12 hours at 4° C. to block non-specific hybridization. Next, B7330N-HA-transfected COS7 cells were incubated with a rat anti-HA antibody (Roche) at 1:1000 dilution. After washing with PBS(−), transfected-cells were stained by an Alexa488-conjugated anti-rat secondary antibody (Molecular Probe) at 1:1000 dilution. Nuclei were counter-stained with 4',6-diamidino-2-phenylindole dihydrochloride (DAPI). Fluorescent images were obtained under a TCS SP2 AOBS microscope (Leica, Tokyo, Japan).

Generation of Anti-B7330N-Specific Polyclonal Antibodies.

Plasmids designed to express two fragments of B7330N (35-239 a.a.) with His-tagged epitope at their N-terminus and C-terminus was prepared using pET28 vector (Novagen, Madison, Wis.). The recombinant peptide was expressed in *Escherichia coli*, BL21 codon-plus strain (Stratagene, La Jolla, Calif.), and purified using Ni-NTA resin agarose (Qiagen) according to the supplier's protocols. The purified recombinant protein was immunized into rabbits. The immune sera were purified on affinity columns using a recombinant protein (35-239 a.a.) according to standard methodology. Affinity-purified anti-B7330N antibodies were used for western blotting, immunocytostaining and immunohistochemical staining as described below.

Expression of Endogenous B7330N in Breast Cancer Cell Lines

To detect the endogenous B7330N protein in breast cancer cell lines (HBC5, MDA-MB-231, SKBR3, and T47D) and HMEC (human mammary gland epitherial cell), cells were lysed in lysis buffer as described above. The amount of total protein was estimated by protein assay kit (Bio-Rad, Hercules, Calif.). and then mixed with SDS-sample buffer and boiled before loading at 10% SDS-PAGE gel as described above. After electrophoresis, the proteins were blotted onto nitrocellulose membrane (GE Healthcare). Membranes including proteins were blocked by blocking solution and incubated with anti-B7330N polyclonal antibody for detection of endogenous B7330N protein. Finally the membrane was incubated with HRP conjugated secondary antibody and protein bands were visualized by ECL detection reagents (GE Healthcare). Beta-actin was examined to serve as a loading control.

To further examine the subcellular localization of endogenous B7330N protein in breast cancer cell-line, T47D, we seeded the cells at $1\times10^5$ cells per well (Lab-Tek II chamber slide, Nalgen Nunc International, Naperville, Ill.). 24 hours after incubation, cells were fixed with PBS(−) containing 4% paraformaldehyde for 15 min, and rendered permeable with PBS (−) containing 0.1% Triton X-100 at 4° C. for 2.5 min. Subsequently, the cells were covered with 3% BSA in PBS (−) at 4° C. for 12 hours to block non-specific hybridization followed by incubation with a rabbit anti-B7330N polyclonal antibody diluted at 1:1000. After washing with PBS (−), the cells were stained by an Alexa488-conjugated anti-rabbit secondary antibody (Molecular Probe, Eugene, Oreg.) diluted at 1:1000. Nuclei were counter-stained with 4',6'-diamidine-2'-phenylindole dihydrochloride (DAPI). Fluorescent images were obtained under a TCS SP2 AOBS microscope (Leica, Tokyo, Japan).

Immunohistotochemical Staining

Expression patterns of B7330N protein in breast cancer and normal tissues were investigated as described previously (Kitahara O, et al. Cancer Res 61, 3544-3549 (2001)) using affinity-purified anti-B7330N polyclonal antibody. For investigation of normal organs, we purchased commercially-available tissue sections of heart, lung, liver, kidney and pancreas (Biochain). Briefly, paraffin-embedded specimens were treated with xylene and ethanol, and were blocked by protein-blocking reagent (Dako Cytomation, Carpinteria, Calif.). The anti-B7330N antibody in antibody-diluted solution (1:50) was added and then stained with substrate-chromogen (DAKO liquid DAB chromogen, DakoCytomation). Finally, tissue specimens were stained with hematoxylin to discriminate nucleus from cytoplasm.

Construction of B7330N Specific-siRNA Expression Vector Using psiU6BX3.0

We established a vector-based RNAI system using psiU6BX3.0 siRNA expression vector according to the previous report (WO2004076623). A siRNA expression vector against B7330N (psiU6BX-B7330N) was prepared by cloning of double-stranded oligonucleotides in Table 1 into the BbsI site in the psiU6BX3.0 vector. Control plasmids, psiU6BX-Mock was prepared by of BsiI and Hind III of multiple cloning site in the psiU6BX3.0 vector, respectively.

TABLE-1

Sequences of double-strand oligonucleotides inserted into siRNA expression vector

| | SEQ ID NO |
|---|---|
| psi-U6BX-Mock (control) | |
| 5'-CACCGTGTCTTCAAGCTTGAAGACTA-3' | 14 |
| 5'-AAAATAGTCTTCAAGCTTGAAGACAC-3' | 15 |
| psi-U6BX-si-1 | |
| 5'-CACCGCACTGTTTCAATGCCTTTTTCAAGAGAAAAGGCATTGAAACAGTGC-3' | 16 |
| 5'-AAAAGCACTGTTTCAATGCCTTTTCTCTTGAAAAAGGCATTGAAACAGTGC-3' | 17 |
| psi-U6BX-si-2 | |
| 5'-CACCGAGAAATCCTTCGGTGACATTCAAGAGATGTCACCGAAGGATTTCTC-3' | 20 |
| 5'-AAAAGAGAAATCCTTCGGTGACATCTCTTGAATGTCACCGAAGGATTTCTC-3' | 21 |

The underlines indicate B7330N-specific siRNA sequences

Gene-Silencing Effect of B7330N Specific siRNA

Human breast cancer cells lines, T47D or BT-20 was plated onto 15-cm dishes ($4\times10^6$ cells/dish) and transfected with 16 μg of each psiU6BX-Mock as negative controls and psiU6BX-B7330N using FuGENE6 reagent according to the supplier's recommendations (Roche). 24 hour after transfection, cells are re-seeded again for colony formation assay ($2\times10^6$ cells/10 cm dish), RT-PCR ($2\times10^6$ cells/10 cm dish) and MTT assay ($2\times10^6$ cells/well). We selected the B7330N-introducing cells with medium containing 0.7 mg/ml or 0.6 mg/ml of neomycin (Geneticin, Invitrogen) in T47D or BT-20 cells, respectively. Afterward, we changed medium every two days for 3 weeks. To evaluate the functioning of siRNA, total RNA was extracted from the cells at 7 days after neomycin selection, and then the knockdown effect of siRNAs was confirmed by a semi-quantitative RT-PCR using specific primer sets for B7330N and GAPDH; 5'-ATGGAAATC-CCATCACCATCT-3' (SEQ ID NO; 11) and 5'-GGTTGAG-CACAGGGTACTTTATT-3' (SEQ ID NO; 2) for GAPDH as an internal control, and 5'-GGATGAAACATACCCCATCA-3' (SEQ ID NO; 12) and 5'-ATGACACTAGTGCCCTTGG-3' (SEQ ID NO; 13) for B7330N. Moreover, transfectants expressing siRNAs using T47D or BT-20 cell lines were grown for 28 days in selective media containing neomycin, respectively. After fixation with 4% paraformaldehyde, transfected cells were stained with Giemsa solution to assess colony formation. MTT assays were performed to quantify cell viability. After 10 days of culture in the neomycin-containing medium, MTT solution (3-(4,5-dimethylthiazol-2-yl)-2,5-diphenyl tetrazolium bromide) (Sigma) was added at a concentration of 0.5 mg/ml. Following incubation at 37° C. for 2.5 hours, acid-SDS (0.01 N HCl/10% SDS) was added; the suspension was mixed vigorously and then incubated overnight at 37° C. to dissolve the dark blue crystals. Absorbance at 570 nm was measured with a Microplate Reader 550 (BioRad). To evaluate the functioning of siRNA, total RNA is extracted from cells 7 days after selection, MTT assay is performed at 10 days after selection using Cell Counting Kit-8 (Dojindo) according to manufacture's protocol. Absorbance is measured at 570 nm wavelength with a Microplate Reader 550 (BioRad). For colony formation assay, cells are fixed with 4% paraformaldehyde for 15 min before staining with Giemsa's solution (Merck). Each experiment is triplicated.

Establishment of NIH3T3 Cells Stably Exprssing B7330N.

The full length-B7330N and N476A mutant expression vectors were transfected into NIH3T3 cells using FUGENE6 as describe above. Transfected cells were incubated in the culture medium containing 0.9 mg/ml of geneticin (G418) (Invitrogen). Clonal NIH3T3 cells were subcloned by limiting dilution. Expression and subcellular localization of HA-tagged B7330N were assessed by western blot analysis and immunocytochemistiy using anti-HA monoclonal antibody, respectively. Eventually, several clones were established and designated as WT-B7330N and N476A-B7330N. To investigate growth-promoting effect of wildtype-B7330N or N476A-B7330N, we seeded 5000 cells each of two independent WT-B7330N-NIH3T3 (WT-1, and -2), two independent cells N476A-B7330N-NIH3T3 (N476A-1 and -2) and two independent MOCK-NIH3T3 (Mock-1 and -2) cells, and counted the number of cells by MTT assay everyday for 6 days. These experiments were done in triplicate.

Western Blotting Analysis of Exogenous B7330N

We examined expression of exogenous B7330N protein in COS7 cells, using pCAGGS-B7330N-HA, pCAGGS-N476A-HA or pCAGGS-N611A-HA transfected-COS7 cells and Mock as a negative control, respectively. Cells were lysed in 0.1% NP-40 lysis buffer containing 50 mmol/L Tris-HCl (pH 8.0), 150 mmol/L NaCl, and 0.1% protease cocktail inhibitor III (Calbiochem, San Diego, Calif.). Cell lysates were separated on 8% SDS-polyacrylamide gels and transferred to nitrocellulose membranes, then incubated with rat anti-HA pAb as primary antibody. After incubation with sheep anti-rat IgG-HRP as secondary antibody (Amersham Biosciences), signals were visualized with an ECL kit (Amersham Biosciences). To detect secreted B7330N protein, B7330N-, N476A-, or N611A-transfected COS7 cells were maintained in serum-free medium for 48 hours after transfection and then cultured for 4 days. B7330N protein in cell lysates and condensed culture media were also detected by rat anti-HA-pAb and anti-rat IgG-HRP. β-actin pAb (1:2000 dilution) served as a loading control for proteins (clone AC-15, Sigma-Aldrich, MO). To confirm glycosylation of B7330N protein, cell lysates were also initially prepared as described above without including protease cocktail inhibitor III. Each of 10 μl cell lysate was mixed with 10 μl of lysis buffer and 1 U of N-glycosidase F (Calbiochem, San Diego, Calif.), then incubated for 1 hour at 37° C. The reaction was boiled with the SDS sample buffer.

Autocrine Assay

B7330N-transfected COS7 cells were maintained in FCS-free medium for two days, and then parental COS7 cells were cultivated with or without B7330N in medium to confirm autocrine stimulation of cell growth for 4 days. Effects of B7330N on cell growth were monitored by counting cells with a hemocytometer and MTT assay as described above. The cells ($5\times10^3$ cells/well) were cultured in DMEM containing 0.1% FCS.

Neutralizing Effect by Anti-B7330N Antibody

Effects of anti-B7330N antibody on cell growth were monitored by counting cells with a hemocytometer. Breast cancer cell lines, T47D and HBL-100 were seeded onto 12-well microplates ($5\times10^4$ cells/well) and cultured for 5 days in McCoy's 5A medium containing 1% FBS supplemented with 10.2 μg/mL affinity-purified anti-B7330N pAb, or with PBS(−) as a negative control. Cell numbers were determined as described above.

Results

Identification of B7330N, Designed UDP-N-Acetyl-Alpha-D-Galactosamine: Polypeptide N-Acetelgalactosaminyltransferase 6, as an Up-Related Gene in Breast Cancer Cells When we analyzed gene-expression profiles of cancer cells from pre-menopausal 77 breast cancer patients using a cDNA microarray representing 27,648 human genes, we identified 493 genes that were commonly up-regulated in breast cancer cells. Among them, we focused on B7330N, designed UDP-N-acetyl-alpha-D-galactosamine: polypeptide N-acetylgalactosaminyltransferase 6, GALNT6, is located at chromosome 12q13 with a mRNA transcript 4381 or 4556 bases in length consisting of 11 exons. Expression of B7330N was elevated in 27 of 77 (35%) breast cancer cases which were able to obtain expression data. To confirm the expression pattern of this gene in breast cancers, we performed semi-quantitative RT-PCR analysis using breast cancer cell lines and normal human tissues including normal breast cells. As a result, we found that B7330N whose expression showed the elevated expression in 7 of 12 clinical breast cancer specimens (poorly-differentiated lesions) compared to normal breast ductal cells and other normal tissues (FIG. 1*a*), andy was overexpressed in 7 of 20 breast cancer cell lines (FIG. 1*b*). To further examine the expression pattern of this gene, we performed northern blot analyses with multiple-human tissues and breast cancer cell lines using a cDNA fragment of B7330N as a probe. As a result, we observed that approximately 5 kb transcript was exclusively expressed in normal human placenta, pancreas, stomach and trachea (FIG. 1*c*). When we further examined the expression pattern of these transcripts with breast cancer-northern blot, we found that this transcript was specifically overexpressed in breast cancer cell lines, compared to normal human tissues including mammary gland and bone marrow (FIG. 1*d*).

The GALNT6 gene encodes a 622 amino acids protein which is capable of glycosylating fibronectin peptide in vitro and is expressed in a fibroblast cell line, indicating that it may be involved in the synthesis of oncofetal fibronectin. SMART and PFAM computer prediction shows GALNT6 contains signal peptide, Glycos_transf_2 motif in 180 to 370 residues, and RICIN motif in 496 to 622 residues.

Expression of Exogenous B7330N

Figure 2:
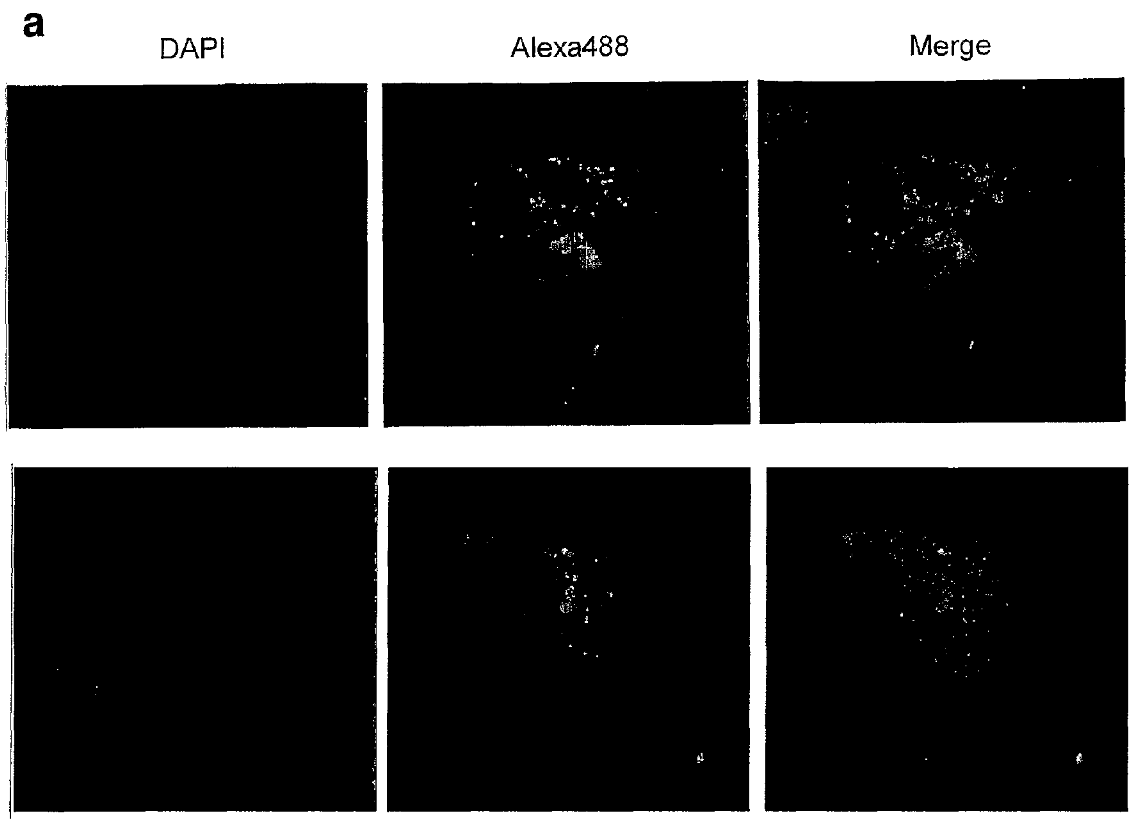
FIG. 2(*a*) shows subcellular localization of exogenous B7330N protein.
Figure 2:
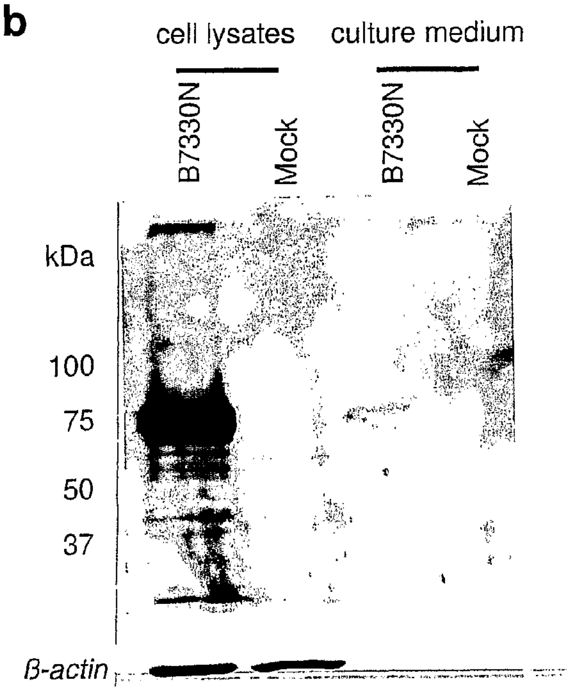

To examine the characterization of B7330N, we investigated the sub-cellular localization of these gene products in mammalian cells. Firstly, when we transiently transfected plasmids expressing B7330N protein (pCAGGS-B7330N-HA) into COS7 cells, immunocytochemical analysis with anti-HA-tag antibody reveals that exogenous B7330N protein was appeared as a granulous pattern in secretion vesicles in all transfected-COS7 cells for 72 hours after transfection (FIG. 2*a*). Then, to examine extracellular secretion of B7330N we performed western blots analysis using cell lysates and culture medium of COS7 cells that had been transiently transfected with a plasmid designed to express B7330N (see Materials and Methods), C-terminal HA-tag antibody detected secretion of the protein into the culture medium (FIG. 2*b*).

The molecular weight of the B7330N products estimated by western blot analysis was found to be larger than that of the predicted size calculated from the cDNA sequences (FIG. 2*b*). Since the primary amino acid sequence of B7330N contains two predicted N-linked glycosylation consensus sequences, to confirm whether these two larger B7330N products were glycosylation, we initially treated the protein with N-glycosydase. As a result, the largest B7330N protein was disappeared in cell lysate, indicating that this protein was glycosylated in mammalian cells (FIG. 3*a*). Subsequently, to determine the N-linked glycosylation site, we established mutant constructs of potential N-glycosylation site of B7330N protein (see Materials and Methods). Then we transfected these plasmids, wild-type, N476A or N611A into COS-7 cells, respectively, and immunoblotted with anti-HA-tag antibody. Interestingly, we observed that the largest band of N476A-transfected cells was disappeared, but wild-type and N611A was not changed in cell lysates, indicating that Asn-476 is putative glycosylation site (FIG. 3*b*). Furthermore, to determine whether glycosylation was necessary for B7330N secretion, we examined whether the exogenous N476A and wild-type B7330N protein into the COS7 cells was secreted to culture medium. Interestingly, exogenous wild-type B7330N was secreted into culture medium, whereas the N476A protein was not detected in culture medium, suggesting glycosylation on Asn-476 of B7330N protein is necessary for secretion (FIG. 3*c*).

Expression of Endogenous B7330N in Breast Cancer Cells.

Figure 7:
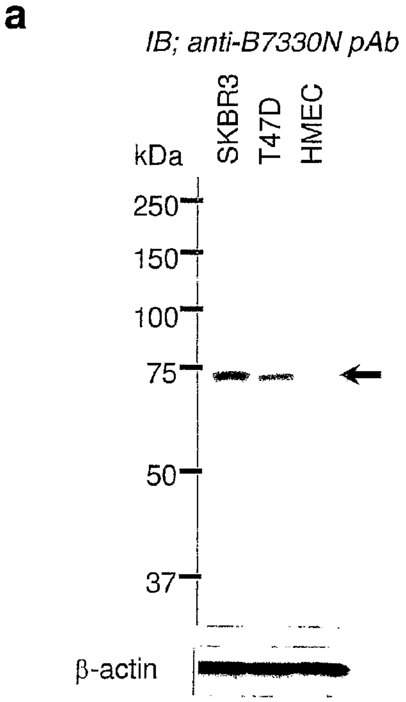
FIG. 7. Expression of B7330N in breast cancer cell-lines and tissue sections. a, Expression of endogenous B7330N protein in breast cancer cell-lines in comparison with HMEC cell-line, examined by Western-blot analysis using affinity purified anti-B7330N antibody. b, Two breast cancer cell-lines, SKBR3 and T47D were immunocytochemically stained with anti-B7330N antibody (red) and DAPI (blue) to discriminate nucleus (see the Materials and Methods). c, immunohistochemical staining results of breast cancer (571T and 164T) and normal breast (425N) tissue sections. Endogenous B7330N protein was stained by use of anti-B7330N pAb. The expression was hardly detected from normal breast tissues (425N), but cancer cells were intensely stained at cytoplasm in all of cancer tissues investigated including intraductal (164T) and papillo-tubular (571T). Representative figures were from microscopic observation with original magnification, upper; ×100 and lower; ×200. d, immunohistochemical staining results of normal vital organs. Endogenous B7330N protein was stained by use of anti B7330N pAb. No expression was observed in any of heart, lung, liver, kidney and pancreas.
Figure 7:
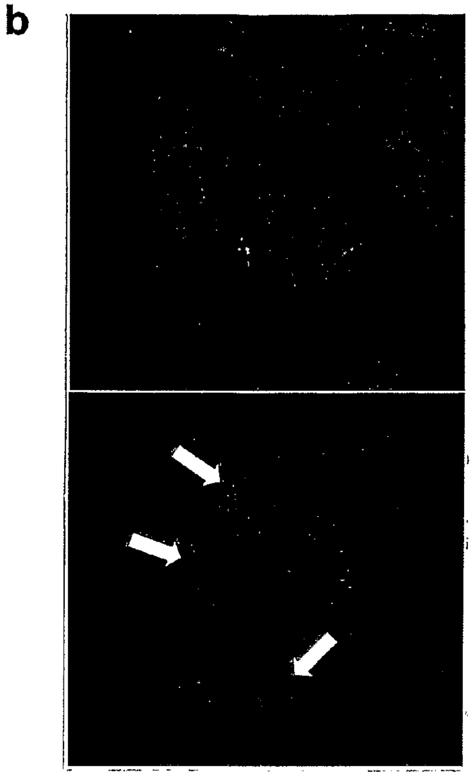
Figure 7:
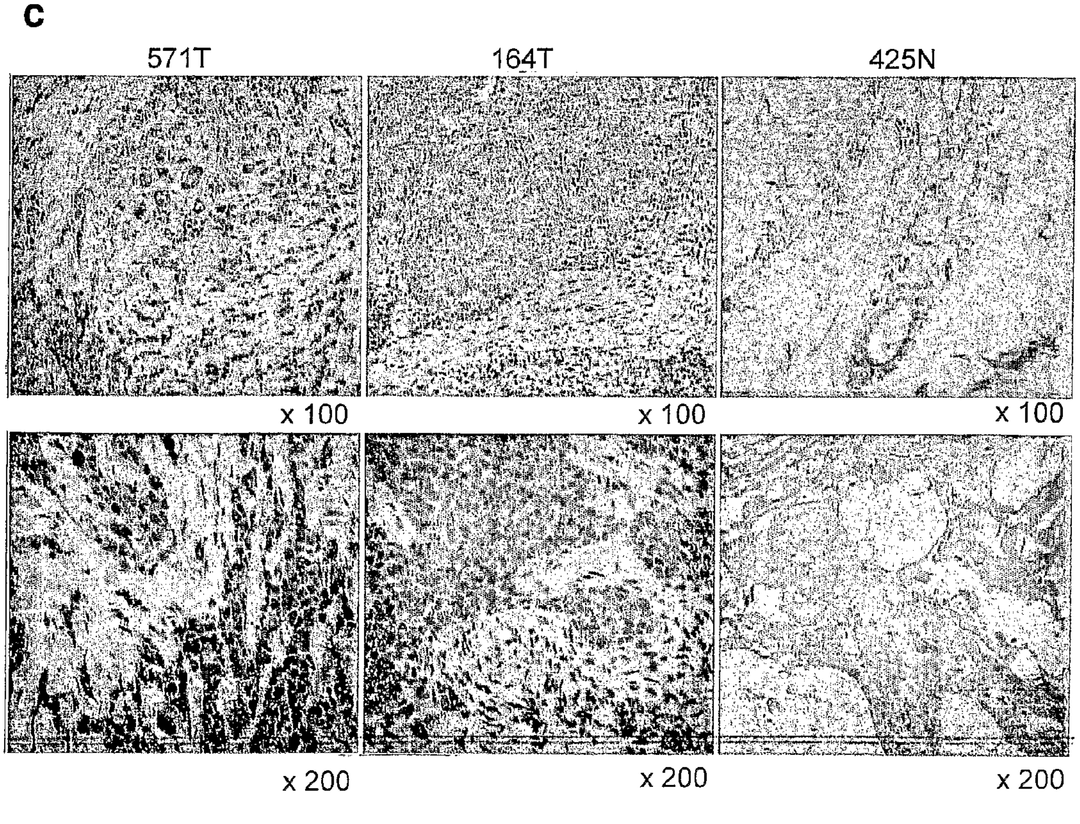
Figure 7:
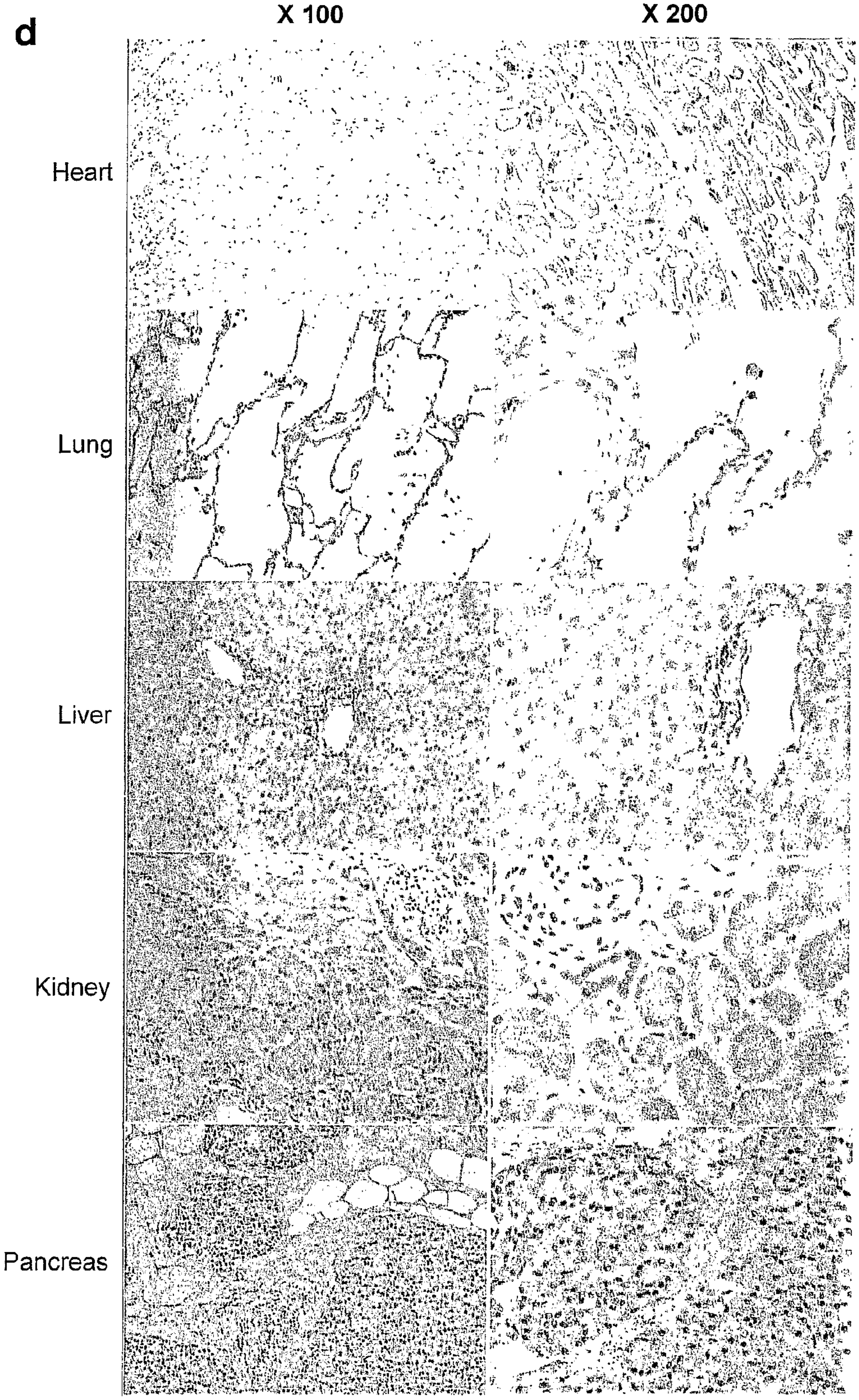

We developed a polyclonal antibody against B7330N, and then investigated endogenous expression of B7330N protein in cell lysates from breast cancer cell-lines, SKBR3, T47D and HMEC (Human Mammalian Epithelial Cell) as a control of the experiments by Western-blot analysis (FIG. 7*a*). Both breast cancer cell-lines showed high levels of B7330N expression, whereas the normal breast epithelial cell-line, IMEC cells showed no expression. Subsequent immunocytochemical analysis of breast cancer cell-lines, T47D using anti-B7330N polyclonal antibody indicated the localization of endogenous B7330N protein was appeared as a granulous pattern in secretion vesicles in breast cancer cells as well as that of exogenously expressed B7330N protein (FIG. 7*b*). To further investigate B7330N expression in breast cancer and normal tissue sections, we performed immunohistochemical staining with anti-B7330N antibody as well. We identified strong staining in the cytoplasm of two different histological subtypes of breast cancer, papillo-tubular carcinoma (571T) and intraductal carcinoma (164T), but its expression was hardly detectable in normal breast tissues (425N) (FIG. 7*c*). Furthermore, in concordance with the results of northern blot analysis, no expression was observed in any of heart, lung, liver, kidney and pancreas (FIG. 7*d*).

Figure 4:
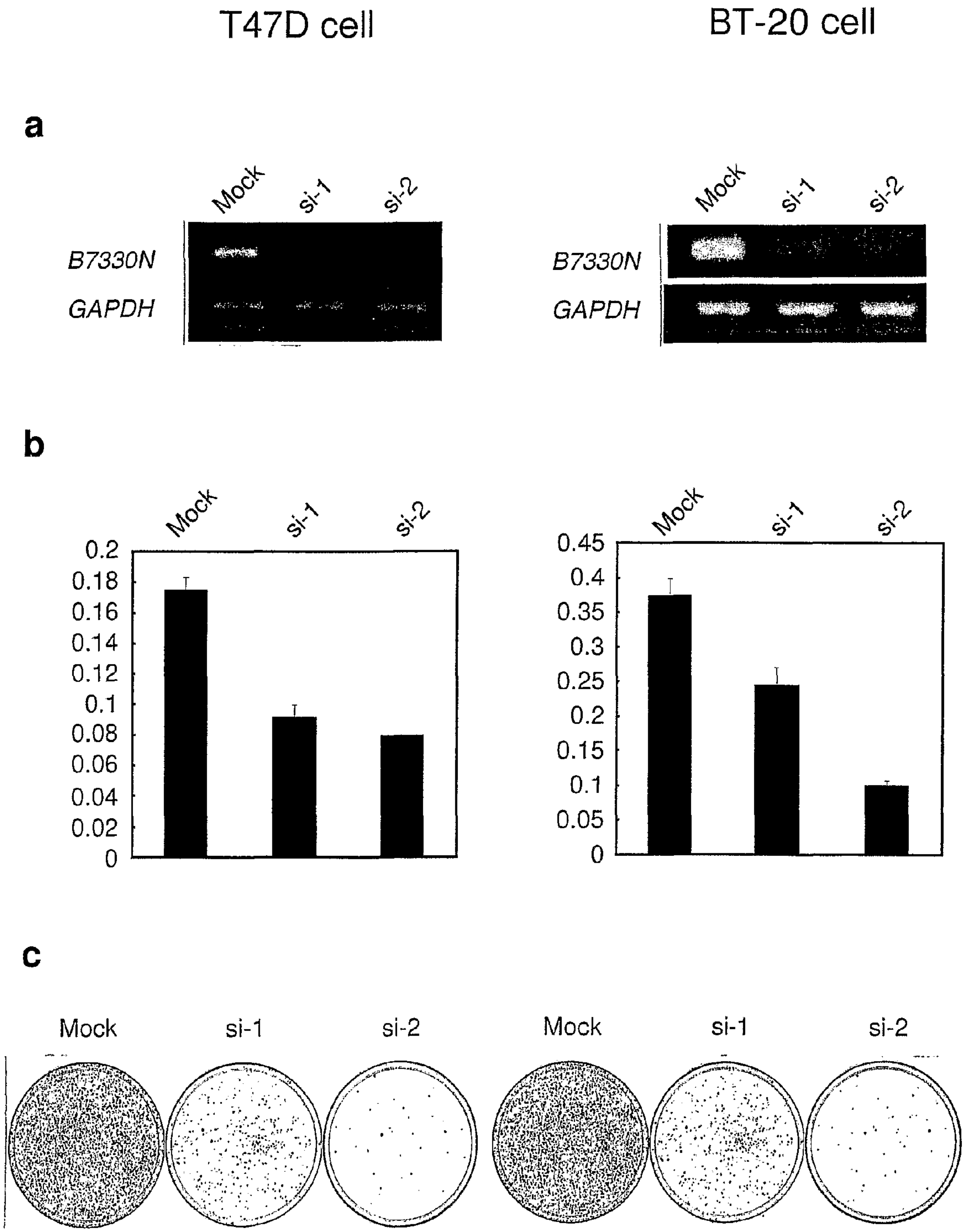
FIG. 4 shows growth-inhibitory effects of small-interfering RNAs (siRNAs) designed to reduce expression of B7330N in T47D cells and BT-20 cells.

Growth-Inhibitory Effects of Small-Interfering RNA (siRNA) Designed to Reduce Expression of B7330N To assess the growth-promoting role of B7330N, we knocked down the expression of endogenous B7330N in breast cancer line T47D and BT-20 (FIG. 4), that have shown the overexpression of B7330N, by means of the mammalian vector-based RNA interference (RNAi) technique (see Materials and Methods). We examined expression levels of B7330N by semi-quantitative RT-PCR experiments. As shown in FIG. 4*a*, among the two siRNA constructs of the gene examined, B7330N-specific siRNAs (si1 and si2) suppressed expression, compared with control siRNA constructs (psiU6BX-Mock). To confirm the cell growth inhibition with B7330N-specific siRNAs, we performed MTT and colony-formation assays, respectively (FIG. 4*b, c*). As a result, introduction of B7330N siRNA constructs suppressed growth of these breast cancer cells, consisting with the result of above reduced expression of this gene. Each result was verified by three independent experiments. Thus, our findings suggest that B7330N has a significant function in the cell growth of the breast cancer.

To further confirm the growth promoting effect of B7330N, we established NIH3T3-derivative cells that stably expressed exogenous B7330N(NIH3T3-WT-B7330N-1, -2 and NIH3T3-N476A-B7330N-1, -2 cells). Western-blot analysis indicated high level of exogenous WT- and N476A-B7330N protein in two derivate clones, respectively (FIG. 8*a*). Subsequent MTT assays showed that three derivative cell lines, NIH3T3-B7330N-1 and -2, grew much faster than cells transfected with mock plasmid (NIH3T3-Mock-1, -2 and -3 cells), whereas N476A-B7330N protein cells grew moderately as compared with WT-B7330N-1, -2 (FIG. 8*b*), indicating B7330N expression was likely to enhance cell growth with expression dependency.

Furthermore, we observed N-glycosylated form in WT-B7330N cells, whereas did not observe it in N476A-B7330N cells (FIG. 8*a*). These results were confirmed that the larger band was disappeared after treatment of N-glycosidase assay as describe above (data not shown).

Autocrine Nature of B7330N Growth Enhancement

We prepared a culture medium containing B7330N protein, derived from the medium used to grow B7330N-overexpressing COS7 cells (FIG. 5*a*), and cultured parental COS7 cells in this medium. This experiment using native B7330N revealed enhanced growth of the COS7 cells (FIG. 5*a*). This result strongly supports our conclusion that B7330N, a secretory molecule, functions as an autocrine growth factor that is essential for proliferation of breast cancer cells. Furthermore, when we added anti-B7330N pAb to culture media supporting breast cancer cell line T47D cells, growth of this cell-line was significantly suppressed as compared with PBS(−) treatment (FIG. 5*b*; left panel), although HBL-100 cells, which do not express B7330N, was not influenced by this treatment of this pAb (FIG. 5*b*; right panel).

Dimerization of B7330N

Since some of glycosyltransferases were reported to form a dimmer in cells (El-Battari A, et al., Glycobiology. 2003; 13(12):941-53), we examined whether B7330N is also able to oligomerize with immunoprecipitation.

When exogenous pCAGGS-B7330N-HA protein was immunoprecipitated with an anti-HA antibody, a western-blot analysis using an anti-HA antibody revealed exogenous B7330N protein in the form a band that corresponded 2-fold of the predicted molecular mass.

Figure 6:
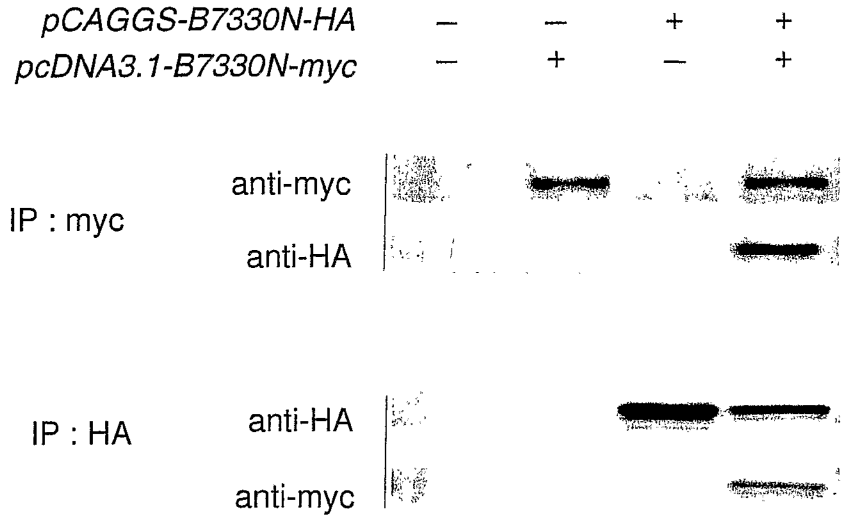
FIG. 6 shows homo-dimerization of B7330N proteins. Immunoprecipitation analysis of Mock and pCAGGS-B7330N-HA and pcDNA3.1-B7330N-myc-transfected COS-7 cells.

To investigate that hypothesis, we designed two kinds of tagged-B7330N constructs to examine homo-oligomerization. pCAGGS-B7330N-HA and pcDNA3.1-B7330N-myc were co-transfected into COS-7 cells and co-immunoprecipitated using anti-HA or anti-myc antibody, respectively. As shown in FIG. 6, using anti-myc antibody to pull down pcDNA3.1-B7330N-myc resulted in co-immunoprecipitation of pCAGGS-B7330N-HA and using anti-HA antibody to pull down pCAGGS-B7330N-HA resulted in co-immunoprecipitation of pcDNA3.1-B7330N-myc. These findings indicated that B7330N is able to constitute a homo-oligomer complex only in living cells.

In this invention, through the precise expression profiles of breast cancer by means of genome wide cDNA microarray, we isolated novel genes, B7330N that were significantly overexpressed in breast cancer cells, compared to normal human tissues.

B7330N, designed to UDP-N-acetyl-alpha-D-galactosamine: polypeptide N-acetylgalactosaminyltransferase 6, GALNT6, is selected for study as its significant elevated-expression in breast cancer. We identified the approximately 5 kb transcripts showed cancer specific expression. We demonstrated treatment of breast cancer cells with siRNA effectively inhibited expression of B7330N and significantly suppressed cell/tumor growth of breast cancer. These findings suggest that B7330N might play key roles in tumor cell growth proliferation, and might be promising targets for development of anti-cancer drugs.

Discussion

In this report, through the precise expression profiles of breast cancer by means of genome wide cDNA microarray, we isolated novel genes, B7330N that were significantly overexpressed in breast cancer cells, compared to normal human tissues. Furthermore, we demonstrated treatment of breast cancer cells with siRNA effectively inhibited expression of target gene, B7330N and significantly suppressed cell/tumor growth of breast cancer. These findings suggest that B7330N might play key roles in tumor cell growth proliferation, and might be promising targets for development of anti-cancer drugs.

B7330N, designed to UDP-N-acetyl-alpha-D-galactosamine: polypeptide N-acetylgalactosaminyltransferase 6, GALNT6, is selected for study as its significant elevated-expression in breast cancer. We identified the approximately 5 kb transcripts showed cancer specific expression. We demonstrated treatment of breast cancer cells with siRNA effectively inhibited expression of B7330N and significantly suppressed cell/tumor growth of breast cancer. These findings suggest that B7330N might play key roles in tumor cell growth proliferation, and might be promising targets for development of anti-cancer drugs.

INDUSTRIAL APPLICABILITY

The expression of human genes B7330N is markedly elevated in breast cancer as compared to non-cancerous breast duct epithelium. Accordingly, this gene is useful as a diagnostic marker of breast cancer and the proteins encoded thereby are useful in diagnostic assays of breast cancer.

The present inventors have also shown that the expression of novel protein B7330N promotes cell growth whereas cell growth is suppressed by small interfering RNAs corresponding to the B7330N gene. These findings show that B7330N protein stimulates oncogenic activity. Thus, each of these novel oncoproteins is a useful target for the development of anti-cancer pharmaceuticals. For example, agents that block the expression of B7330N, or prevent its activity find therapeutic utility as anti-cancer agents, particularly anti-cancer agents for the treatment of breast cancers. Examples of such agents include antisense oligonucleotides, small interfering RNAs, and ribozymes against the B7330N gene, and antibodies that recognize B7330N.

While the invention has been described in detail and with reference to specific embodiments thereof, it will be apparent to one skilled in the art that various changes and modifications can be made therein without departing from the spirit and scope of the invention.

The invention claimed is:

1. A method of screening for a compound for treating breast cancer, said method comprising the steps of:

(a) contacting a test compound with a polypeptide selected from the group consisting of:

(1) a polypeptide comprising the amino acid sequence of SEQ ID NO: 27;

(2) a polypeptide encoded by the nucleotide sequence of SEQ ID NO: 26 which is expressed endogenously or exogenously by cells;

(b) detecting a biological activity of the polypeptide of step (a), wherein the biological activity is acetylgalactosaminyltransferase; and (c) identifying a compound that suppresses the biological activity of the polypeptide in comparison with the biological activity detected in the absence of the test compound;

(d) culturing animal cells which express the polypeptide defined in (a) (1) in the presence of the test compound identified in step (c);

(e) detecting the promotion of proliferation of the animal cells; and (f) identifying a compound that suppresses the promotion of proliferation of the animal cells in comparison with that detected in the absence of the test compound, as a candidate compound to be used for the treatment of breast cancer.

2. The method of claim 1, wherein the proliferation of the animal cells is detected by measuring colony forming activity.

* * * * *

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 1

cgaccacttt gtcaagctca                                              20


<210> SEQ ID NO 2
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 2

ggttgagcac agggtacttt att                                          23


<210> SEQ ID NO 3
```

-continued

<211> LENGTH: 24
<212> TYPE: DNA
<213> ORGANISM: Artificial
<220> FEATURE:
<223> OTHER INFORMATION: An artificially synthesized primer sequence for RT-PCR

<400> SEQUENCE: 3
gagtccaggt aagtgaatct gtcc 24

<210> SEQ ID NO 4
<211> LENGTH: 22
<212> TYPE: DNA
<213> ORGANISM: Artificial
<220> FEATURE:
<223> OTHER INFORMATION: An artificially synthesized primer sequence for RT-PCR

<400> SEQUENCE: 4
atttccaccg agacctctca tc 22

<210> SEQ ID NO 5
<211> LENGTH: 25
<212> TYPE: DNA
<213> ORGANISM: Artificial
<220> FEATURE:
<223> OTHER INFORMATION: An artificially synthesized primer sequence for RT-PCR

<400> SEQUENCE: 5
cggaattcat gaggctcctc cgcag 25

<210> SEQ ID NO 6
<211> LENGTH: 30
<212> TYPE: DNA
<213> ORGANISM: Artificial
<220> FEATURE:
<223> OTHER INFORMATION: An artificially synthesized primer sequence for RT-PCR

<400> SEQUENCE: 6
ccgctcgagg acaaagagcc acaactgatg 30

<210> SEQ ID NO 7
<211> LENGTH: 35
<212> TYPE: DNA
<213> ORGANISM: Artificial
<220> FEATURE:
<223> OTHER INFORMATION: An artificially synthesized primer sequence for PCR

<400> SEQUENCE: 7
acaactgcac tgtcacgcct tttcctggta cctgc 35

<210> SEQ ID NO 8
<211> LENGTH: 35
<212> TYPE: DNA
<213> ORGANISM: Artificial
<220> FEATURE:
<223> OTHER INFORMATION: An artificially synthesized primer sequence for PCR

<400> SEQUENCE: 8
gcaggtacca ggaaaaggcg tgacagtgca gttgt 35

<210> SEQ ID NO 9
<211> LENGTH: 29

-continued

<212> TYPE: DNA
<213> ORGANISM: Artificial
<220> FEATURE:
<223> OTHER INFORMATION: An artificially synthesized primer sequence for PCR

<400> SEQUENCE: 9
catggccccc tgcgcaccca gtgaccccc 29

<210> SEQ ID NO 10
<211> LENGTH: 29
<212> TYPE: DNA
<213> ORGANISM: Artificial
<220> FEATURE:
<223> OTHER INFORMATION: An artificially synthesized primer sequence for PCR

<400> SEQUENCE: 10
gggggtcact gggtgcgcag ggggccatg 29

<210> SEQ ID NO 11
<211> LENGTH: 21
<212> TYPE: DNA
<213> ORGANISM: Artificial
<220> FEATURE:
<223> OTHER INFORMATION: An artificially synthesized primer sequence for RT-PCR

<400> SEQUENCE: 11
atggaaatcc catcaccatc t 21

<210> SEQ ID NO 12
<211> LENGTH: 20
<212> TYPE: DNA
<213> ORGANISM: Artificial
<220> FEATURE:
<223> OTHER INFORMATION: An artificially synthesized primer sequence for RT-PCR

<400> SEQUENCE: 12
ggatgaaaca taccccatca 20

<210> SEQ ID NO 13
<211> LENGTH: 19
<212> TYPE: DNA
<213> ORGANISM: Artificial
<220> FEATURE:
<223> OTHER INFORMATION: An artificially synthesized primer sequence for RT-PCR

<400> SEQUENCE: 13
atgacactag tgcccttgg 19

<210> SEQ ID NO 14
<211> LENGTH: 26
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 14
caccgtgtct tcaagcttga agacta 26

<210> SEQ ID NO 15
<211> LENGTH: 26
<212> TYPE: DNA

-continued

<213> ORGANISM: Artificial
<220> FEATURE:
<223> OTHER INFORMATION: An artificially synthesized oligonucleotide for
constructing of siRNA expression vector

<400> SEQUENCE: 15
aaaatagtct tcaagcttga agacac 26

<210> SEQ ID NO 16
<211> LENGTH: 51
<212> TYPE: DNA
<213> ORGANISM: Artificial
<220> FEATURE:
<223> OTHER INFORMATION: An artificially synthesized oligonucleotide for
constructing of siRNA expression vector

<400> SEQUENCE: 16
caccgcactg tttcaatgcc tttttcaaga gaaaaggcat tgaaacagtg c 51

<210> SEQ ID NO 17
<211> LENGTH: 51
<212> TYPE: DNA
<213> ORGANISM: Artificial
<220> FEATURE:
<223> OTHER INFORMATION: An artificially synthesized oligonucleotide for
constructing of siRNA expression vector

<400> SEQUENCE: 17
aaaagcactg tttcaatgcc ttttctcttg aaaaaggcat tgaaacagtg c 51

<210> SEQ ID NO 18
<211> LENGTH: 19
<212> TYPE: DNA
<213> ORGANISM: Artificial
<220> FEATURE:
<223> OTHER INFORMATION: target sequence for siRNA

<400> SEQUENCE: 18
gcactgtttc aatgccttt 19

<210> SEQ ID NO 19
<211> LENGTH: 47
<212> TYPE: DNA
<213> ORGANISM: Artificial
<220> FEATURE:
<223> OTHER INFORMATION: siRNA hairpin design

<400> SEQUENCE: 19
gcactgtttc aatgcctttt tcaagagaaa aggcattgaa acagtgc 47

<210> SEQ ID NO 20
<211> LENGTH: 51
<212> TYPE: DNA
<213> ORGANISM: Artificial
<220> FEATURE:
<223> OTHER INFORMATION: An artificially synthesized oligonucleotide for
constructing of siRNA expression vector

<400> SEQUENCE: 20
caccgagaaa tccttcggtg acattcaaga gatgtcaccg aaggatttct c 51

<210> SEQ ID NO 21
<211> LENGTH: 51
<212> TYPE: DNA
<213> ORGANISM: Artificial
<220> FEATURE:
<223> OTHER INFORMATION: An artificially synthesized oligonucleotide for constructing of siRNA expression vector

<400> SEQUENCE: 21
aaaagagaaa tccttcggtg acatctcttg aatgtcaccg aaggatttct c 51

<210> SEQ ID NO 22
<211> LENGTH: 19
<212> TYPE: DNA
<213> ORGANISM: Artificial
<220> FEATURE:
<223> OTHER INFORMATION: target sequence for siRNA

<400> SEQUENCE: 22
gagaaatcct tcggtgaca 19

<210> SEQ ID NO 23
<211> LENGTH: 47
<212> TYPE: DNA
<213> ORGANISM: Artificial
<220> FEATURE:
<223> OTHER INFORMATION: siRNA hairpin design

<400> SEQUENCE: 23
gagaaatcct tcggtgacat tcaagagatg tcaccgaagg atttctc 47

<210> SEQ ID NO 24
<211> LENGTH: 4381
<212> TYPE: DNA
<213> ORGANISM: Homo sapiens
<220> FEATURE:
<221> NAME/KEY: CDS
<222> LOCATION: (1)..(1866)

<400> SEQUENCE: 24

```
atg agg ctc ctc cgc aga cgc cac atg ccc ctg cgc ctg gcc atg gtg       48
Met Arg Leu Leu Arg Arg Arg His Met Pro Leu Arg Leu Ala Met Val
1               5                   10                  15

ggc tgc gcc ttt gtg ctc ttc ctc ttc ctc ctg cat agg gat gtg agc       96
Gly Cys Ala Phe Val Leu Phe Leu Phe Leu Leu His Arg Asp Val Ser
            20                  25                  30

agc aga gag gag gcc aca gag aag ccg tgg ctg aag tcc ctg gtg agc      144
Ser Arg Glu Glu Ala Thr Glu Lys Pro Trp Leu Lys Ser Leu Val Ser
        35                  40                  45

cgg aag gat cac gtc ctg gac ctc atg ctg gag gcc atg aac aac ctt      192
Arg Lys Asp His Val Leu Asp Leu Met Leu Glu Ala Met Asn Asn Leu
    50                  55                  60

aga gat tca atg ccc aag ctc caa atc agg gct cca gaa gcc cag cag      240
Arg Asp Ser Met Pro Lys Leu Gln Ile Arg Ala Pro Glu Ala Gln Gln
65                  70                  75                  80

act ctg ttc tcc ata aac cag tcc tgc ctc cct ggg ttc tat acc cca      288
Thr Leu Phe Ser Ile Asn Gln Ser Cys Leu Pro Gly Phe Tyr Thr Pro
                85                  90                  95

gct gaa ctg aag ccc ttc tgg gaa cgg cca cca cag gac ccc aat gcc      336
Ala Glu Leu Lys Pro Phe Trp Glu Arg Pro Pro Gln Asp Pro Asn Ala
            100                 105                 110

cct ggg gca gat gga aaa gca ttt cag aag agc aag tgg acc ccc ctg      384
Pro Gly Ala Asp Gly Lys Ala Phe Gln Lys Ser Lys Trp Thr Pro Leu
        115                 120                 125

gag acc cag gaa aag gaa gaa ggc tat aag aag cac tgt ttc aat gcc      432
Glu Thr Gln Glu Lys Glu Glu Gly Tyr Lys Lys His Cys Phe Asn Ala
    130                 135                 140

ttt gcc agc gac cgg atc tcc ctg cag agg tcc ctg ggg cca gac acc      480
Phe Ala Ser Asp Arg Ile Ser Leu Gln Arg Ser Leu Gly Pro Asp Thr
```

-continued

```
145                 150                 155                 160

cga cca cct gag tgt gtg gac cag aag ttc cgg cgc tgc ccc cca ctg      528
Arg Pro Pro Glu Cys Val Asp Gln Lys Phe Arg Arg Cys Pro Pro Leu
                165                 170                 175

gcc acc acc agc gtg atc att gtg ttc cac aac gaa gcc tgg tcc aca      576
Ala Thr Thr Ser Val Ile Ile Val Phe His Asn Glu Ala Trp Ser Thr
            180                 185                 190

ctg ctg cga aca gtg tac agc gtc cta cac acc acc cct gcc atc ttg      624
Leu Leu Arg Thr Val Tyr Ser Val Leu His Thr Thr Pro Ala Ile Leu
        195                 200                 205

ctc aag gag atc ata ctg gtg gat gat gcc agc aca gag gag cac cta      672
Leu Lys Glu Ile Ile Leu Val Asp Asp Ala Ser Thr Glu Glu His Leu
    210                 215                 220

aag gag aag ctg gag cag tac gtg aag cag ctg cag gtg gtg agg gtg      720
Lys Glu Lys Leu Glu Gln Tyr Val Lys Gln Leu Gln Val Val Arg Val
225                 230                 235                 240

gtg cgg cag gag gag cgg aag ggg ctg atc acc gcc cgg ctg ctg ggg      768
Val Arg Gln Glu Glu Arg Lys Gly Leu Ile Thr Ala Arg Leu Leu Gly
                245                 250                 255

gcc agc gtg gca cag gcg gag gtg ctc acg ttc ctg gat gcc cac tgt      816
Ala Ser Val Ala Gln Ala Glu Val Leu Thr Phe Leu Asp Ala His Cys
            260                 265                 270

gag tgc ttc cac ggc tgg ctg gag ccc ctc ctg gct cga atc gct gag      864
Glu Cys Phe His Gly Trp Leu Glu Pro Leu Leu Ala Arg Ile Ala Glu
        275                 280                 285

gac aag aca gtg gtg gtg agc cca gac atc gtc acc atc gac ctt aat      912
Asp Lys Thr Val Val Val Ser Pro Asp Ile Val Thr Ile Asp Leu Asn
    290                 295                 300

act ttt gag ttc gcc aag ccc gtc cag agg ggc aga gtc cat agc cga      960
Thr Phe Glu Phe Ala Lys Pro Val Gln Arg Gly Arg Val His Ser Arg
305                 310                 315                 320

ggc aac ttt gac tgg agc ctg acc ttc ggc tgg gaa aca ctt cct cca     1008
Gly Asn Phe Asp Trp Ser Leu Thr Phe Gly Trp Glu Thr Leu Pro Pro
                325                 330                 335

cat gag aag cag agg cgc aag gat gaa acc tac ccc atc aaa tcc ccg     1056
His Glu Lys Gln Arg Arg Lys Asp Glu Thr Tyr Pro Ile Lys Ser Pro
            340                 345                 350

acg ttt gct ggt ggc ctc ttc tcc atc tcc aag tcc tac ttt gag cac     1104
Thr Phe Ala Gly Gly Leu Phe Ser Ile Ser Lys Ser Tyr Phe Glu His
        355                 360                 365

atc ggt acc tat gat aat cag atg gag atc tgg gga ggg gag aac gtg     1152
Ile Gly Thr Tyr Asp Asn Gln Met Glu Ile Trp Gly Gly Glu Asn Val
    370                 375                 380

gaa atg tcc ttc cgg gtg tgg cag tgt ggg ggc cag ctg gag atc atc     1200
Glu Met Ser Phe Arg Val Trp Gln Cys Gly Gly Gln Leu Glu Ile Ile
385                 390                 395                 400

ccc tgc tct gtc gta ggc cat gtg ttc cgg acc aag agc ccc cac acc     1248
Pro Cys Ser Val Val Gly His Val Phe Arg Thr Lys Ser Pro His Thr
                405                 410                 415

ttc ccc aag ggc act agt gtc att gct cgc aat caa gtg cgc ctg gca     1296
Phe Pro Lys Gly Thr Ser Val Ile Ala Arg Asn Gln Val Arg Leu Ala
            420                 425                 430

gag gtc tgg atg gac agc tac aag aag att ttc tat agg aga aat ctg     1344
Glu Val Trp Met Asp Ser Tyr Lys Lys Ile Phe Tyr Arg Arg Asn Leu
        435                 440                 445

cag gca gca aag atg gcc caa gag aaa tcc ttc ggt gac att tcg gaa     1392
Gln Ala Ala Lys Met Ala Gln Glu Lys Ser Phe Gly Asp Ile Ser Glu
    450                 455                 460

cga ctg cag ctg agg gaa caa ctg cac tgt cac aac ttt tcc tgg tac     1440
```

-continued

```
Arg Leu Gln Leu Arg Glu Gln Leu His Cys His Asn Phe Ser Trp Tyr
465                 470                 475                 480

ctg cac aat gtc tac cca gag atg ttt gtt cct gac ctg acg ccc acc     1488
Leu His Asn Val Tyr Pro Glu Met Phe Val Pro Asp Leu Thr Pro Thr
                485                 490                 495

ttc tat ggt gcc atc aag aac ctc ggc acc aac caa tgc ctg gat gtg     1536
Phe Tyr Gly Ala Ile Lys Asn Leu Gly Thr Asn Gln Cys Leu Asp Val
            500                 505                 510

ggt gag aac aac cgc ggg ggg aag ccc ctc atc atg tac tcc tgc cac     1584
Gly Glu Asn Asn Arg Gly Gly Lys Pro Leu Ile Met Tyr Ser Cys His
        515                 520                 525

ggc ctt ggc ggc aac cag tac ttt gag tac aca act cag agg gac ctt     1632
Gly Leu Gly Gly Asn Gln Tyr Phe Glu Tyr Thr Thr Gln Arg Asp Leu
    530                 535                 540

cgc cac aac atc gca aag cag ctg tgt cta cat gtc agc aag ggt gct     1680
Arg His Asn Ile Ala Lys Gln Leu Cys Leu His Val Ser Lys Gly Ala
545                 550                 555                 560

ctg ggc ctt ggg agc tgt cac ttc act ggc aag aat agc cag gtc ccc     1728
Leu Gly Leu Gly Ser Cys His Phe Thr Gly Lys Asn Ser Gln Val Pro
                565                 570                 575

aag gac gag gaa tgg gaa ttg gcc cag gat cag ctc atc agg aac tca     1776
Lys Asp Glu Glu Trp Glu Leu Ala Gln Asp Gln Leu Ile Arg Asn Ser
            580                 585                 590

gga tct ggt acc tgc ctg aca tcc cag gac aaa aag cca gcc atg gcc     1824
Gly Ser Gly Thr Cys Leu Thr Ser Gln Asp Lys Lys Pro Ala Met Ala
        595                 600                 605

ccc tgc aat ccc agt gac ccc cat cag ttg tgg ctc ttt gtc             1866
Pro Cys Asn Pro Ser Asp Pro His Gln Leu Trp Leu Phe Val
    610                 615                 620

taggacccag atcatcccca gagagagccc ccacaagctc ctcaggaaac aggattgctg   1926

atgtctggga acctgatcac cagcttctct ggaggccgta aagatggatt tctaaaccca   1986

ctgggtggca aggcaggacc ttcctaatcc ttgcaacaac attgggccca ttttctttcc   2046

ttcacaccga tggaagagac cattaggaca tatatttagc ctagcgtttt cctgttctag   2106

aaatagaggc tcccaaagta gggaaggcag ctgggggagg gttcagggca gcaatgctga   2166

gttcaagaaa agtacttcag gctgggcaca gtggctcatg cctgaaatcc tagcactttg   2226

ggaagacaat gtgggagaat ggcttgagcc caggagttca agaccggcct gagcaacata   2286

gtgaggatcc catctctacg cccaccctcc ccccggcaaa aaaaaaaagc tgggtatggt   2346

ggcttatgcc tgtagtcgca gctactcaga aggctgaggt gggaggattg cttgttcccc   2406

ggaggttgaa gctacagtga gccttgattg tgtcactgca ctccagcctg ggcaacaggt   2466

aagactctgt ctcaaaaaaa aacaaaaaag aagaagaaaa gtacttctac agccatgtcc   2526

tattccttga tcatccaaag cacctgcaga gtccagtgaa atgatatatt ctggctgggc   2586

acagtggctc acacctgtaa tcctagcact ttgggaggcc aaggcaggtg gatcacctga   2646

ggtcagaagt ttgaaaccag cctggactac atggtgaaac tccatctcta ctaaaagtac   2706

aaaaattagc tgggcatgat ggcacgcacc tgcagtccca gctacttggg aggctgaggc   2766

aggagaatca ctcgaaccca ggaggcagag gttgcagtga gccaagacag caccattgca   2826

ccccagcctg agcaacaaga gcgaaactcc atctcaggaa aaaaaaaaaa aaaaaaagta   2886

tattctaaca gacagatcag aggtctaaga gatcctccct tgctattatt acctgaagtc   2946

tgtagaactg tttacagata tctccttgac aggtgtcctt tatcttactt tatctgtaca   3006

gtaatcctgt gagaaagaca ggacagaaac cactgtgcct attttacaga tacgaaaact   3066
```

-continued gagacacagg taaaggggct tgtctgtagt cccatagcta gcagatggct ggagccaaga 3126 ctgaggctcg ttcttcaatg ctgagccagg gctccttccg ctgcaccaca agaacgctag 3186 accactcgcc accagccttc tcattccctc ttcctccatt ctaatcattt ctagctggct 3246 ggcctccaca gagcatagga aaacagccag ggccgggcac ggtggctcat gcctgtaatc 3306 tcaacactct gggaggccga gccgggtgga taacctgagg tcaggaattc gagaccagcc 3366 tggccaacat ggtaaaaccc catctctact aaaaatataa aaattagcca ggcatggtgg 3426 cgcacacctg taatcccagc tactcaagag gctgaggcag gagaattgct taaatctggg 3486 aggcggaagt tgcagtgagc caagatcgcg ccactgaact ccagcctagg caacaagagc 3546 aaaactccat ctccaaaaaa aagaaaggaa aaacagggcc aggtagccat tgtggagaga 3606 gcacacttag gaatcctggg atgttagtgt taaaagaaag ctcctggagc cagtgattct 3666 caggtttgtc ccagaaccct tttttctaag ccccatataa aaggtagatt aaaaaaacaa 3726 agtagcatga gtgaaattga gagagggaca ggtaatgcct tccagcccct aacttctaac 3786 aatctggaag cacaacgtga aaatcacgta gcccaaccct atcattttca tattatgaaa 3846 ctgagtccag gtaagtgaat ctgtccaagg tcacccagca aggtatcagt agccctgagg 3906 gtaaggactc tgataaggct cgggagggtc ctggaaagcc tgaggcggca ggaagagtgt 3966 gcagagttga gcgtgtctgg aaggctgatc cactgctggg cccacatcaa agcccccatg 4026 gggagcagac ccgactgcac atggctcttt tgctggaaga agagcatggc tgcgcagagg 4086 actaaaattt catctgggaa ggcttctttt gactgtcagt agcaggatgt caccagatga 4146 gggtgctatg ggaccacagc tgtctttgtt cccattgcaa ctcaaccctg cgggaggccg 4206 cctacatccc tgagagcctt ctggagccta cagaggagac attggccagc caaaaggaaa 4266 ggagtggcca gggtacgacc tggagtaggg aagggaaaaa gttcccggaa agaagagaat 4326 tggatgagag gtctcagtgg aaataaaggt tttctggcat tggtcaagga aactc 4381

<210> SEQ ID NO 25
<211> LENGTH: 622
<212> TYPE: PRT
<213> ORGANISM: Homo sapiens

<400> SEQUENCE: 25

Met Arg Leu Leu Arg Arg Arg His Met Pro Leu Arg Leu Ala Met Val
1               5                   10                  15

Gly Cys Ala Phe Val Leu Phe Leu Phe Leu Leu His Arg Asp Val Ser
            20                  25                  30

Ser Arg Glu Glu Ala Thr Glu Lys Pro Trp Leu Lys Ser Leu Val Ser
        35                  40                  45

Arg Lys Asp His Val Leu Asp Leu Met Leu Glu Ala Met Asn Asn Leu
    50                  55                  60

Arg Asp Ser Met Pro Lys Leu Gln Ile Arg Ala Pro Glu Ala Gln Gln
65                  70                  75                  80

Thr Leu Phe Ser Ile Asn Gln Ser Cys Leu Pro Gly Phe Tyr Thr Pro
                85                  90                  95

Ala Glu Leu Lys Pro Phe Trp Glu Arg Pro Pro Gln Asp Pro Asn Ala
            100                 105                 110

Pro Gly Ala Asp Gly Lys Ala Phe Gln Lys Ser Lys Trp Thr Pro Leu
        115                 120                 125

Glu Thr Gln Glu Lys Glu Glu Gly Tyr Lys Lys His Cys Phe Asn Ala
    130                 135                 140

-continued

```
Phe Ala Ser Asp Arg Ile Ser Leu Gln Arg Ser Leu Gly Pro Asp Thr
145                 150                 155                 160

Arg Pro Pro Glu Cys Val Asp Gln Lys Phe Arg Arg Cys Pro Pro Leu
                165                 170                 175

Ala Thr Thr Ser Val Ile Ile Val Phe His Asn Glu Ala Trp Ser Thr
            180                 185                 190

Leu Leu Arg Thr Val Tyr Ser Val Leu His Thr Thr Pro Ala Ile Leu
        195                 200                 205

Leu Lys Glu Ile Ile Leu Val Asp Asp Ala Ser Thr Glu Glu His Leu
    210                 215                 220

Lys Glu Lys Leu Glu Gln Tyr Val Lys Gln Leu Gln Val Val Arg Val
225                 230                 235                 240

Val Arg Gln Glu Glu Arg Lys Gly Leu Ile Thr Ala Arg Leu Leu Gly
                245                 250                 255

Ala Ser Val Ala Gln Ala Glu Val Leu Thr Phe Leu Asp Ala His Cys
            260                 265                 270

Glu Cys Phe His Gly Trp Leu Glu Pro Leu Leu Ala Arg Ile Ala Glu
        275                 280                 285

Asp Lys Thr Val Val Val Ser Pro Asp Ile Val Thr Ile Asp Leu Asn
    290                 295                 300

Thr Phe Glu Phe Ala Lys Pro Val Gln Arg Gly Arg Val His Ser Arg
305                 310                 315                 320

Gly Asn Phe Asp Trp Ser Leu Thr Phe Gly Trp Glu Thr Leu Pro Pro
                325                 330                 335

His Glu Lys Gln Arg Arg Lys Asp Glu Thr Tyr Pro Ile Lys Ser Pro
            340                 345                 350

Thr Phe Ala Gly Gly Leu Phe Ser Ile Ser Lys Ser Tyr Phe Glu His
        355                 360                 365

Ile Gly Thr Tyr Asp Asn Gln Met Glu Ile Trp Gly Gly Glu Asn Val
    370                 375                 380

Glu Met Ser Phe Arg Val Trp Gln Cys Gly Gly Gln Leu Glu Ile Ile
385                 390                 395                 400

Pro Cys Ser Val Val Gly His Val Phe Arg Thr Lys Ser Pro His Thr
                405                 410                 415

Phe Pro Lys Gly Thr Ser Val Ile Ala Arg Asn Gln Val Arg Leu Ala
            420                 425                 430

Glu Val Trp Met Asp Ser Tyr Lys Lys Ile Phe Tyr Arg Arg Asn Leu
        435                 440                 445

Gln Ala Ala Lys Met Ala Gln Glu Lys Ser Phe Gly Asp Ile Ser Glu
    450                 455                 460

Arg Leu Gln Leu Arg Glu Gln Leu His Cys His Asn Phe Ser Trp Tyr
465                 470                 475                 480

Leu His Asn Val Tyr Pro Glu Met Phe Val Pro Asp Leu Thr Pro Thr
                485                 490                 495

Phe Tyr Gly Ala Ile Lys Asn Leu Gly Thr Asn Gln Cys Leu Asp Val
            500                 505                 510

Gly Glu Asn Asn Arg Gly Gly Lys Pro Leu Ile Met Tyr Ser Cys His
        515                 520                 525

Gly Leu Gly Gly Asn Gln Tyr Phe Glu Tyr Thr Thr Gln Arg Asp Leu
    530                 535                 540

Arg His Asn Ile Ala Lys Gln Leu Cys Leu His Val Ser Lys Gly Ala
545                 550                 555                 560

Leu Gly Leu Gly Ser Cys His Phe Thr Gly Lys Asn Ser Gln Val Pro
```

-continued

```
                565                 570                 575

Lys Asp Glu Glu Trp Glu Leu Ala Gln Asp Gln Leu Ile Arg Asn Ser
            580                 585                 590

Gly Ser Gly Thr Cys Leu Thr Ser Gln Asp Lys Lys Pro Ala Met Ala
        595                 600                 605

Pro Cys Asn Pro Ser Asp Pro His Gln Leu Trp Leu Phe Val
    610                 615                 620


<210> SEQ ID NO 26
<211> LENGTH: 4556
<212> TYPE: DNA
<213> ORGANISM: Homo sapiens
<220> FEATURE:
<221> NAME/KEY: CDS
<222> LOCATION: (207)..(2072)

<400> SEQUENCE: 26

aacaggccct gctgtgaggg accacgaggc agtgccagga tgaaagagtt ggagtaacct      60

aggtgattct gagtgaatca gtcaggaggc cttcctggag gggctgagg ccccagcttg    120

tggccaccac aacgtatcaa gctatctcca gggttgggct caggactcag agctgacgca    180

gctggggtgc cccttggttc tggagg atg agg ctc ctc cgc aga cgc cac atg    233
                             Met Arg Leu Leu Arg Arg Arg His Met
                             1               5

ccc ctg cgc ctg gcc atg gtg ggc tgc gcc ttt gtg ctc ttc ctc ttc      281
Pro Leu Arg Leu Ala Met Val Gly Cys Ala Phe Val Leu Phe Leu Phe
10                  15                  20                  25

ctc ctg cat agg gat gtg agc agc aga gag gag gcc aca gag aag ccg      329
Leu Leu His Arg Asp Val Ser Ser Arg Glu Glu Ala Thr Glu Lys Pro
                30                  35                  40

tgg ctg aag tcc ctg gtg agc cgg aag gat cac gtc ctg gac ctc atg      377
Trp Leu Lys Ser Leu Val Ser Arg Lys Asp His Val Leu Asp Leu Met
            45                  50                  55

ctg gag gcc atg aac aac ctt aga gat tca atg ccc aag ctc caa atc      425
Leu Glu Ala Met Asn Asn Leu Arg Asp Ser Met Pro Lys Leu Gln Ile
        60                  65                  70

agg gct cca gaa gcc cag cag act ctg ttc tcc ata aac cag tcc tgc      473
Arg Ala Pro Glu Ala Gln Gln Thr Leu Phe Ser Ile Asn Gln Ser Cys
    75                  80                  85

ctc cct ggg ttc tat acc cca gct gaa ctg aag ccc ttc tgg gaa cgg      521
Leu Pro Gly Phe Tyr Thr Pro Ala Glu Leu Lys Pro Phe Trp Glu Arg
90                  95                  100                 105

cca cca cag gac ccc aat gcc cct ggg gca gat gga aaa gca ttt cag      569
Pro Pro Gln Asp Pro Asn Ala Pro Gly Ala Asp Gly Lys Ala Phe Gln
                110                 115                 120

aag agc aag tgg acc ccc ctg gag acc cag gaa aag gaa gaa ggc tat      617
Lys Ser Lys Trp Thr Pro Leu Glu Thr Gln Glu Lys Glu Glu Gly Tyr
            125                 130                 135

aag aag cac tgt ttc aat gcc ttt gcc agc gac cgg atc tcc ctg cag      665
Lys Lys His Cys Phe Asn Ala Phe Ala Ser Asp Arg Ile Ser Leu Gln
        140                 145                 150

agg tcc ctg ggg cca gac acc cga cca cct gag tgt gtg gac cag aag      713
Arg Ser Leu Gly Pro Asp Thr Arg Pro Pro Glu Cys Val Asp Gln Lys
    155                 160                 165

ttc cgg cgc tgc ccc cca ctg gcc acc acc agc gtg atc att gtg ttc      761
Phe Arg Arg Cys Pro Pro Leu Ala Thr Thr Ser Val Ile Ile Val Phe
170                 175                 180                 185

cac aac gaa gcc tgg tcc aca ctg ctg cga aca gtg tac agc gtc cta      809
His Asn Glu Ala Trp Ser Thr Leu Leu Arg Thr Val Tyr Ser Val Leu
                190                 195                 200
```

-continued

```
cac acc acc cct gcc atc ttg ctc aag gag atc ata ctg gtg gat gat      857
His Thr Thr Pro Ala Ile Leu Leu Lys Glu Ile Ile Leu Val Asp Asp
            205                 210                 215

gcc agc aca gag gag cac cta aag gag aag ctg gag cag tac gtg aag      905
Ala Ser Thr Glu Glu His Leu Lys Glu Lys Leu Glu Gln Tyr Val Lys
        220                 225                 230

cag ctg cag gtg gtg agg gtg gtg cgg cag gag gag cgg aag ggg ttg      953
Gln Leu Gln Val Val Arg Val Val Arg Gln Glu Glu Arg Lys Gly Leu
    235                 240                 245

atc acc gcc cgg ctg ctg ggg gcc agc gtg gca cag gcg gag gtg ctc     1001
Ile Thr Ala Arg Leu Leu Gly Ala Ser Val Ala Gln Ala Glu Val Leu
250                 255                 260                 265

acg ttc ctg gat gcc cac tgt gag tgc ttc cac ggc tgg ctg gag ccc     1049
Thr Phe Leu Asp Ala His Cys Glu Cys Phe His Gly Trp Leu Glu Pro
                270                 275                 280

ctc ctg gct cga atc gct gag gac aag aca gtg gtg gtg agc cca gac     1097
Leu Leu Ala Arg Ile Ala Glu Asp Lys Thr Val Val Val Ser Pro Asp
            285                 290                 295

atc gtc acc atc gac ctt aat act ttt gag ttc gcc aag ccc gtc cag     1145
Ile Val Thr Ile Asp Leu Asn Thr Phe Glu Phe Ala Lys Pro Val Gln
        300                 305                 310

agg ggc aga gtc cat agc cga ggc aac ttt gac tgg agc ctg acc ttc     1193
Arg Gly Arg Val His Ser Arg Gly Asn Phe Asp Trp Ser Leu Thr Phe
    315                 320                 325

ggc tgg gaa aca ctt cct cca cat gag aag cag agg cgc aag gat gaa     1241
Gly Trp Glu Thr Leu Pro Pro His Glu Lys Gln Arg Arg Lys Asp Glu
330                 335                 340                 345

aca tac ccc atc aaa tcc ccg acg ttt gct ggt ggc ctc ttc tcc atc     1289
Thr Tyr Pro Ile Lys Ser Pro Thr Phe Ala Gly Gly Leu Phe Ser Ile
                350                 355                 360

ccc aag tcc tac ttt gag cac atc ggt acc tat gat aat cag atg gag     1337
Pro Lys Ser Tyr Phe Glu His Ile Gly Thr Tyr Asp Asn Gln Met Glu
            365                 370                 375

atc tgg gga ggg gag aac gtg gaa atg tcc ttc cgg gtg tgg cag tgt     1385
Ile Trp Gly Gly Glu Asn Val Glu Met Ser Phe Arg Val Trp Gln Cys
        380                 385                 390

ggg ggc cag ctg gag atc atc ccc tgc tct gtc gta ggc cat gtg ttc     1433
Gly Gly Gln Leu Glu Ile Ile Pro Cys Ser Val Val Gly His Val Phe
    395                 400                 405

cgg acc aag agc ccc cac acc ttc ccc aag ggc act agt gtc att gct     1481
Arg Thr Lys Ser Pro His Thr Phe Pro Lys Gly Thr Ser Val Ile Ala
410                 415                 420                 425

cgc aat caa gtg cgc ctg gca gag gtc tgg atg gac agc tac aag aag     1529
Arg Asn Gln Val Arg Leu Ala Glu Val Trp Met Asp Ser Tyr Lys Lys
                430                 435                 440

att ttc tat agg aga aat ctg cag gca gca aag atg gcc caa gag aaa     1577
Ile Phe Tyr Arg Arg Asn Leu Gln Ala Ala Lys Met Ala Gln Glu Lys
            445                 450                 455

tcc ttc ggt gac att tcg gaa cga ctg cag ctg agg gaa caa ctg cac     1625
Ser Phe Gly Asp Ile Ser Glu Arg Leu Gln Leu Arg Glu Gln Leu His
        460                 465                 470

tgt cac aac ttt tcc tgg tac ctg cac aat gtc tac cca gag atg ttt     1673
Cys His Asn Phe Ser Trp Tyr Leu His Asn Val Tyr Pro Glu Met Phe
    475                 480                 485

gtt cct gac ctg acg ccc acc ttc tat ggt gcc atc aag aac ctc ggc     1721
Val Pro Asp Leu Thr Pro Thr Phe Tyr Gly Ala Ile Lys Asn Leu Gly
490                 495                 500                 505

acc aac caa tgc ctg gat gtg ggt gag aac aac cgc ggg ggg aag ccc     1769
Thr Asn Gln Cys Leu Asp Val Gly Glu Asn Asn Arg Gly Gly Lys Pro
```

-continued

```
                510                 515                 520

ctc atc atg tac tcc tgc cac ggc ctt ggc ggc aac cag tac ttt gag     1817
Leu Ile Met Tyr Ser Cys His Gly Leu Gly Gly Asn Gln Tyr Phe Glu
            525                 530                 535

tac aca act cag agg gac ctt cgc cac aac atc gca aag cag ctg tgt     1865
Tyr Thr Thr Gln Arg Asp Leu Arg His Asn Ile Ala Lys Gln Leu Cys
        540                 545                 550

cta cat gtc agc aag ggt gct ctg ggc ctt ggg agc tgt cac ttc act     1913
Leu His Val Ser Lys Gly Ala Leu Gly Leu Gly Ser Cys His Phe Thr
    555                 560                 565

ggc aag aat agc cag gtc ccc aag gac gag gaa tgg gaa ttg gcc cag     1961
Gly Lys Asn Ser Gln Val Pro Lys Asp Glu Glu Trp Glu Leu Ala Gln
570                 575                 580                 585

gat cag ctc atc agg aac tca gga tct ggt acc tgc ctg aca tcc cag     2009
Asp Gln Leu Ile Arg Asn Ser Gly Ser Gly Thr Cys Leu Thr Ser Gln
                590                 595                 600

gac aaa aag cca gcc atg gcc ccc tgc aat ccc agt gac ccc cat cag     2057
Asp Lys Lys Pro Ala Met Ala Pro Cys Asn Pro Ser Asp Pro His Gln
            605                 610                 615

ttg tgg ctc ttt gtc taggacccag atcatcccca gagagagccc ccacaagctc     2112
Leu Trp Leu Phe Val
        620

ctcaggaaac aggattgctg atgtctggga acctgatcac cagcttctct ggaggccgta   2172

aagatggatt tctaaaccca ctgggtggca aggcaggacc ttcctaatcc ttgcaacaac   2232

attgggccca ttttctttcc ttcacaccga tggaagagac cattaggaca tatatttagc   2292

ctagcgtttt cctgttctag aaatagaggc tcccaaagta gggaaggcag ctgggggagg   2352

gttcagggca gcaatgctga gttcaagaaa agtacttcag gctgggcaca gtggctcatg   2412

cctgaaatcc tagcactttg ggaagacaat gtgggagaat ggcttgagcc caggagttca   2472

agaccggcct gagcaacata gtgaggatcc catctctacg cccaccctcc ccccggcaaa   2532

aaaaaaagct gggtatggtg gcttatgcct gtagtcgcag ctactcagaa ggctgaggtg   2592

ggaggattgc ttgttccccg gaggttgaag ctacagtgag ccttgattgt gtcactgcac   2652

tccagcctgg gcaacaggta agactctgtc tcaaaaaaaa aacaaaaaag aagaagaaaa   2712

gtacttctac agccatgtcc tattccttga tcatccaaag cacctgcaga gtccagtgaa   2772

atgatatatt ctggctgggc acagtggctc acacctgtaa tcctagcact ttgggaggcc   2832

aaggcaggtg gatcacctga ggtcagaagt ttgaaaccag cctggactac atggtgaaac   2892

tccatctcta ctaaaagtac aaaaattagc tgggcatgat ggcacgcacc tgcagtccca   2952

gctacttggg aggctgaggc aggagaatca ctcgaaccca ggaggcagag gttgcagtga   3012

gccaagacag caccattgca ccccagcctg agcaacaaga gcgaaactcc atctcaggaa   3072

aaaaaaaaaa aaaaaaagta tattctaaca gacagatcag aggtctaaga gatcctccct   3132

tgctattatt acctgaagtc tgtagaactg tttacagata tctccttgac aggtgtcctt   3192

tatcttactt tatctgtaca gtaatcctgt gagaaagaca ggacagaaac cactgtgcct   3252

attttacaga tacgaaaact gagacacagg taaaggggct tgtctgtagt cccatagcta   3312

gcagatggct ggagccaaga ctgaggctcg ttcttcaatg ctgagccagg gctccttccg   3372

ctgcaccaca agaacgctag accactcgcc accagccttc tcattccctc ttcctccatt   3432

ctaatcattt ctagctggct ggcctccaca gagcatagga aaacagccag ggccgggcac   3492

ggtggctcat gcctgtaatc tcaacactct gggaggccga gccgggtgga taacctgagg   3552

tcaggaattc gagaccagcc tggccaacat ggtaaaaccc catctctact aaaaatataa   3612
```

-continued

```
aaattagcca ggcatggtgg cgcacacctg taatcccagc tactcaagag gctgaggcag   3672

gagaattgct taaatctggg aggcggaagt tgcagtgagc caagatcgcg ccactgaact   3732

ccagcctagg caacaagagc aaaactccat ctccaaaaaa aagaaaggaa aaacagggcc   3792

aggtagccat tgtggagaga gcacacttag gaatcctggg atgttagtgt taaaagaaag   3852

ctcctggagc cagtgattct caggtttgtc ccagaaccct tttttctaag ccccatataa   3912

aaggtagatt aaaaaaacaa agtagcatga gtgaaattga gagagggaca ggtaatgcct   3972

tccagcccct aacttctaac aatctggaag cacaacgtga aaatcacgta gcccaaccct   4032

atcattttca tattatgaaa ctgagtccag gtaagtgaat ctgtccaagg tcacccagca   4092

aggtatcagt agccctgagg gtaaggactc tgataaggct cgggagggtc ctggaaagcc   4152

tgaggcggca ggaagagtgt gcagagttga gcgtgtctgg aaggctgatc cactgctggg   4212

cccacatcaa agcccccatg gggagcagac ccgactgcac atggctcttt tgctggaaga   4272

agagcatggc tgcgcagagg actaaaattt catctgggaa ggcttctttt gactgtcagt   4332

agcaggatgt caccagatga gggtgctatg ggaccacagc tgtctttgtt cccattgcaa   4392

ctcaaccctg cgggaggccg cctacatccc tgagagcctt ctggagccta cagaggagac   4452

attggccagc caaaaggaaa ggagtggcca gggtacgacc tggagtaggg aagggaaaaa   4512

gttcccggaa agaagagaat tggatgagag gtctcagtgg aaat                     4556
```

```
<210> SEQ ID NO 27
<211> LENGTH: 622
<212> TYPE: PRT
<213> ORGANISM: Homo sapiens

<400> SEQUENCE: 27

Met Arg Leu Leu Arg Arg Arg His Met Pro Leu Arg Leu Ala Met Val
1               5                   10                  15

Gly Cys Ala Phe Val Leu Phe Leu Phe Leu Leu His Arg Asp Val Ser
            20                  25                  30

Ser Arg Glu Glu Ala Thr Glu Lys Pro Trp Leu Lys Ser Leu Val Ser
        35                  40                  45

Arg Lys Asp His Val Leu Asp Leu Met Leu Glu Ala Met Asn Asn Leu
    50                  55                  60

Arg Asp Ser Met Pro Lys Leu Gln Ile Arg Ala Pro Glu Ala Gln Gln
65                  70                  75                  80

Thr Leu Phe Ser Ile Asn Gln Ser Cys Leu Pro Gly Phe Tyr Thr Pro
                85                  90                  95

Ala Glu Leu Lys Pro Phe Trp Glu Arg Pro Pro Gln Asp Pro Asn Ala
            100                 105                 110

Pro Gly Ala Asp Gly Lys Ala Phe Gln Lys Ser Lys Trp Thr Pro Leu
        115                 120                 125

Glu Thr Gln Glu Lys Glu Glu Gly Tyr Lys Lys His Cys Phe Asn Ala
    130                 135                 140

Phe Ala Ser Asp Arg Ile Ser Leu Gln Arg Ser Leu Gly Pro Asp Thr
145                 150                 155                 160

Arg Pro Pro Glu Cys Val Asp Gln Lys Phe Arg Arg Cys Pro Pro Leu
                165                 170                 175

Ala Thr Thr Ser Val Ile Ile Val Phe His Asn Glu Ala Trp Ser Thr
            180                 185                 190

Leu Leu Arg Thr Val Tyr Ser Val Leu His Thr Thr Pro Ala Ile Leu
        195                 200                 205
```

-continued

```
Leu Lys Glu Ile Ile Leu Val Asp Asp Ala Ser Thr Glu Glu His Leu
    210                 215                 220

Lys Glu Lys Leu Glu Gln Tyr Val Lys Gln Leu Gln Val Val Arg Val
225                 230                 235                 240

Val Arg Gln Glu Glu Arg Lys Gly Leu Ile Thr Ala Arg Leu Leu Gly
                245                 250                 255

Ala Ser Val Ala Gln Ala Glu Val Leu Thr Phe Leu Asp Ala His Cys
            260                 265                 270

Glu Cys Phe His Gly Trp Leu Glu Pro Leu Leu Ala Arg Ile Ala Glu
        275                 280                 285

Asp Lys Thr Val Val Val Ser Pro Asp Ile Val Thr Ile Asp Leu Asn
    290                 295                 300

Thr Phe Glu Phe Ala Lys Pro Val Gln Arg Gly Arg Val His Ser Arg
305                 310                 315                 320

Gly Asn Phe Asp Trp Ser Leu Thr Phe Gly Trp Glu Thr Leu Pro Pro
                325                 330                 335

His Glu Lys Gln Arg Arg Lys Asp Glu Thr Tyr Pro Ile Lys Ser Pro
            340                 345                 350

Thr Phe Ala Gly Gly Leu Phe Ser Ile Pro Lys Ser Tyr Phe Glu His
        355                 360                 365

Ile Gly Thr Tyr Asp Asn Gln Met Glu Ile Trp Gly Gly Glu Asn Val
    370                 375                 380

Glu Met Ser Phe Arg Val Trp Gln Cys Gly Gly Gln Leu Glu Ile Ile
385                 390                 395                 400

Pro Cys Ser Val Val Gly His Val Phe Arg Thr Lys Ser Pro His Thr
                405                 410                 415

Phe Pro Lys Gly Thr Ser Val Ile Ala Arg Asn Gln Val Arg Leu Ala
            420                 425                 430

Glu Val Trp Met Asp Ser Tyr Lys Lys Ile Phe Tyr Arg Arg Asn Leu
        435                 440                 445

Gln Ala Ala Lys Met Ala Gln Glu Lys Ser Phe Gly Asp Ile Ser Glu
    450                 455                 460

Arg Leu Gln Leu Arg Glu Gln Leu His Cys His Asn Phe Ser Trp Tyr
465                 470                 475                 480

Leu His Asn Val Tyr Pro Glu Met Phe Val Pro Asp Leu Thr Pro Thr
                485                 490                 495

Phe Tyr Gly Ala Ile Lys Asn Leu Gly Thr Asn Gln Cys Leu Asp Val
            500                 505                 510

Gly Glu Asn Asn Arg Gly Gly Lys Pro Leu Ile Met Tyr Ser Cys His
        515                 520                 525

Gly Leu Gly Gly Asn Gln Tyr Phe Glu Tyr Thr Thr Gln Arg Asp Leu
    530                 535                 540

Arg His Asn Ile Ala Lys Gln Leu Cys Leu His Val Ser Lys Gly Ala
545                 550                 555                 560

Leu Gly Leu Gly Ser Cys His Phe Thr Gly Lys Asn Ser Gln Val Pro
                565                 570                 575

Lys Asp Glu Glu Trp Glu Leu Ala Gln Asp Gln Leu Ile Arg Asn Ser
            580                 585                 590

Gly Ser Gly Thr Cys Leu Thr Ser Gln Asp Lys Lys Pro Ala Met Ala
        595                 600                 605

Pro Cys Asn Pro Ser Asp Pro His Gln Leu Trp Leu Phe Val
    610                 615                 620
```